United States Patent
Itescu et al.

(10) Patent No.: US 12,257,270 B2
(45) Date of Patent: *Mar. 25, 2025

(54) TREATMENT OF IMMUNE DISORDERS

(71) Applicant: Mesoblast International Sarl, Meyrin (CH)

(72) Inventors: Silviu Itescu, Melbourne (AU); Paul Simmons, Melbourne (AU)

(73) Assignee: MESOBLAST INTERNATIONAL SARL, Meyrin (CH)

( * ) Notice: Subject to any disclaimer, the term of this patent is extended or adjusted under 35 U.S.C. 154(b) by 167 days.

This patent is subject to a terminal disclaimer.

(21) Appl. No.: 17/870,936

(22) Filed: Jul. 22, 2022

(65) Prior Publication Data

US 2023/0141347 A1 May 11, 2023

Related U.S. Application Data

(60) Continuation of application No. 16/828,121, filed on Mar. 24, 2020, now Pat. No. 11,406,669, which is a division of application No. 15/317,673, filed as application No. PCT/EP2015/062138 on Jun. 1, 2015, now Pat. No. 10,624,930.

(30) Foreign Application Priority Data

Jun. 10, 2014 (AU) .................. 2014902194
Jun. 13, 2014 (AU) .................. 2014902257

(51) Int. Cl.
| A61K 35/28 | (2015.01) |
| A61K 9/00 | (2006.01) |
| A61K 35/545 | (2015.01) |
| A61K 38/17 | (2006.01) |
| A61K 38/18 | (2006.01) |
| A61P 3/10 | (2006.01) |
| A61P 29/00 | (2006.01) |

(52) U.S. Cl.
CPC ............ *A61K 35/28* (2013.01); *A61K 9/0019* (2013.01); *A61K 35/545* (2013.01); *A61K 38/17* (2013.01); *A61K 38/18* (2013.01); *A61P 3/10* (2018.01); *A61P 29/00* (2018.01)

(58) Field of Classification Search
CPC ...... A61K 35/28; A61K 35/545; A61K 38/17; A61K 38/18; A61P 29/10; A61P 29/00
See application file for complete search history.

(56) References Cited

U.S. PATENT DOCUMENTS

| 2010/0124569 A1 | 5/2010 | Abbot |
| 2017/0106023 A1 | 4/2017 | Itescu et al. |

FOREIGN PATENT DOCUMENTS

| CN | 102 899 293 A | 1/2013 | |
| CN | 102899293 | 1/2013 | |
| CN | 106459913 | 2/2017 | |
| EP | 2824175 A2 * | 1/2015 | ............ A61K 35/28 |
| JP | 2008-514188 | 5/2008 | |
| JP | 2011-067175 | 4/2011 | |
| JP | 2017-512842 | 5/2017 | |
| JP | 2021-28337 | 2/2021 | |
| WO | WO-2010005527 A1 * | 1/2010 | ............ A61K 35/28 |
| WO | WO 2012/051210 | 4/2012 | |
| WO | WO 2013/082543 | 6/2013 | |
| WO | WO 2015/155187 | 10/2015 | |
| WO | WO 2015/189063 | 12/2015 | |

OTHER PUBLICATIONS

International Search Report and Written Opinion of the International Searching Authority in connection with PCT/EP2015/062138.
J. Xu, et al., "Mesenchymal stem cell-based angiopoietin-1 gene therapy for acute lung injury induced by lipopolysaccharide in mice", The Journal of Pathology, Mar. 11, 2008, pp. 472-481, 214, Wiley InterScience.
Yaojiong Wu, et al., "Mesenchymal Stem Cells Enhance Wound Healing Through Differentiation and Angiogenesis", Stem Cells, Oct. 1, 2007, pp. 2648-2659, vol. 25, No. 10, Alphamed Press, Dayton, OH, US.
Hye Jin Jin, et al., "Comparative Analysis of Human Mesenchymal Stem Cells from Bone Marrow, Adipose Tissue, and Umbilical Cord Blood as Sources of Cell Therapy", International Journal of Molecular Sciences, Sep. 3, 2013, pp. 17986-18001, vol. 14, No. 9.
Sandra S. Edwards, et al., "Functional analysis reveals angiogenic potential of human mesenchymal stem cells from Wharton's jelly in dermal regeneration", Angiogenesis, Apr. 13, 2014, pp. 851-866, vol. 17, No. 4, Kluwer, Dordrecht, NL.
Darwin J. Prockop, et al., "Mesenchymal Stem/Stromal Cells (MSCs): Role as Guardians of Inflammation", Molecular Therapy, Oct. 18, 2011, pp. 14-20, vol. 20, No. 1.
Guihua Liu, et al., "Correction of Diabetic Erectile Dysfunction with Adipose Derived Stem Cells Modified with the Vascular Endothelial Growth Factor Gene in a Rodent Diabetic Model", PLOS ONE, Aug. 30, 2013, pp. 1-13, vol. 8, No. 8.
Written Opinion issued Sep. 11, 2017 by the Intellectual Property Office of Singapore in connection with counterpart Singaporean Patent Application No. SG 11201609993Y.
Sorrentino A. et al., "Isolation and characterization of CD146+ multipotent mesenchymal stromal cells", Experimental Hematology, May 27, 2008, vol. 36, No. 8, pp. 1035-1046.
12. Fang Xh. et al., "Allogenic Human Mesenchymal Stem Cells Restore Epithelial Protein Permeability in Cultured Human Alveolar Type II Cells by Secretion of Angiopoietin-1", J Biol Chem., Jun. 16, 2010, vol. 285, No. 34, pp. 26211-26222.
Angelo, Laura S., and Razelle Kurzrock. "Vascular endothelial growth factor and its relationship to inflammatory mediators." Clinical cancer research 13.10 (2007): 2825-2830.

(Continued)

Primary Examiner — Ruth A Davis
(74) Attorney, Agent, or Firm — John P. White

(57) ABSTRACT

The present disclosure relates to stem cells which express high levels of Angeopoetin-1 (Ang1) and uses thereof in inhibiting M1-type macrophage production and treating inflammatory disease such as diabetes.

10 Claims, 32 Drawing Sheets

(56) References Cited

OTHER PUBLICATIONS

Bartaula-Brevik, S., et al. "Secretome of Mesenchymal Stem Cells Grown in Hypoxia Accelerates Wound Healing and Vessel Formation." (2017).
Brindle, Nicholas PJ, Pipsa Saharinen, and Kari Alitalo. "Signaling and functions of angiopoietin-1 in vascular protection." Circulation research 98.8 (2006): 1014-1023.
Donath, Marc Y., and Steven E. Shoelson. "Type 2 diabetes as an inflammatory disease." Nature reviews immunology 11.2 (2011): 98-107.
Edwards, Sandra S., et al. "Functional analysis reveals angiogenic potential of human mesenchymal stem cells from Wharton's jelly in dermal regeneration." Angiogenesis 17 (2014): 851-866.
Fang, Xiaohui, et al. "Allogeneic human mesenchymal stem cells restore epithelial protein permeability in cultured human alveolar type II Cells by Secretion of Angiopoietin-1." Journal of Biological Chemistry 285.34 (2010): 26211-26222.
Gordon, Siamon, and Philip R. Taylor. "Monocyte and macrophage heterogeneity." Nature reviews immunology 5.12 (2005): 953-964.
Gronthos, Stan, and Paul J. Simmons. "The growth factor requirements of STRO-1-positive human bone marrow stromal precursors under serum-deprived conditions in vitro." (1995): 929-940.
Gronthos, Stan, et al. "Molecular and cellular characterisation of highly purified stromal stem cells derived from human bone marrow." Journal of cell science 116.9 (2003): 1827-1835.
Chant, A. D., P. Magnussen, and C. Kershaw. "Support hose and varicose veins." British Medical Journal (Clinical research ed.) 290.6463 (1985): 204.
Hsieh, Jui-Yu, et al. "Mesenchymal stem cells from human umbilical cord express preferentially secreted factors related to neuroprotection, neurogenesis, and angiogenesis." PloS one 8.8 (2013): e72604.
Hu, Xinyang, et al. "Transplantation of hypoxia-preconditioned mesenchymal stem cells improves infarcted heart function via enhanced survival of implanted cells and angiogenesis." The Journal of thoracic and cardiovascular surgery 135.4 (2008): 799-808.
Jin, Hye Jin, et al. "Comparative analysis of human mesenchymal stem cells from bone marrow, adipose tissue, and umbilical cord blood as sources of cell therapy." International journal of molecular sciences 14.9 (2013): 17986-18001.
Kim, Injune, et al. "Angiopoietin-1 reduces VEGF-stimulated leukocyte adhesion to endothelial cells by reducing ICAM-1, VCAM-1, and E-selectin expression." Circulation research 89.6 (2001): 477-479.
Levey, Andrew S., et al. "A new equation to estimate glomerular filtration rate." Annals of internal medicine 150.9 (2009): 604-612.
Liu, Guihua, et al. "Correction of diabetic erectile dysfunction with adipose derived stem cells modified with the vascular endothelial growth factor gene in a rodent diabetic model." PloS one 8.8 (2013): e72790.
Mantovani, Alberto, et al. "Macrophage polarization: tumor-associated macrophages as a paradigm for polarized M2 mononuclear phagocytes." Trends in immunology 23.11 (2002): 549-555.
Martens, Timothy P., et al. "Mesenchymal lineage precursor cells induce vascular network formation in ischemic myocardium." Nature Clinical Practice Cardiovascular Medicine 3.Suppl 1 (2006): S18-S22.
Murphy, Matthew B., Kathryn Moncivais, and Arnold I. Caplan. "Mesenchymal stem cells: environmentally responsive therapeutics for regenerative medicine." Experimental & molecular medicine 45.11 (2013): e54-e54.
Murukesh, N., Caroline Dive, and Gordon C. Jayson. "Biomarkers of angiogenesis and their role in the development of VEGF inhibitors." British journal of cancer 102.1 (2010): 8-18.
Prockop, Darwin J., and Joo Youn Oh. "Mesenchymal stem/stromal cells (MSCs): role as guardians of inflammation." Molecular therapy 20.1 (2012): 14-20.
Shohara, Ryutaro, et al. "Mesenchymal stromal cells of human umbilical cord Wharton's jelly accelerate wound healing by paracrine mechanisms." Cytotherapy 14.10 (2012): 1171-1181.
Sorrentino, Antonio, et al. "Isolation and characterization of CD146+ multipotent mesenchymal stromal cells." Experimental hematology 36.8 (2008): 1035-1046.
Stanners, C. P., G. L. Eliceiri, and H. Green. "Two types of ribosome in mouse-hamster hybrid cells." Nature New Biology 230.10 (1971): 52-54.
Thorp, B. H., et al. "Type II collagen-immune complex arthritis in sheep: collagen antibodies in serum, synovial fluid and afferent lymph." Clinical and experimental rheumatology 10.2 (1992): 143-150.
Wu, Yaojiong, et al. "Mesenchymal stem cells enhance wound healing through differentiation and angiogenesis." Stem cells 25.10 (2007): 2648-2659.
Xu, J., et al. "Mesenchymal stem cell-based angiopoietin-1 gene therapy for acute lung injury induced by lipopolysaccharide in mice." The Journal of pathology 214.4 (2008): 472-481.
Zannettino, Andrew CW, et al. "The sialomucin CD164 (MGC-24v) is an adhesive glycoprotein expressed by human hematopoietic progenitors and bone marrow stromal cells that serves as a potent negative regulator of hematopoiesis." Blood, The Journal of the American Society of Hematology 92.8 (1998): 2613-2628.

\* cited by examiner

TREATMENT OF IMMUNE DISORDERS

CROSS-REFERENCE TO RELATED APPLICATIONS

This application is a continuation of U.S. Application Ser. No. 16/828,121, filed Mar. 24, 2020, now allowed, which is a divisional of U.S. application Ser. No. 15/317,673, filed Dec. 9, 2016, now U.S. Pat. No. 10,624,930, issued Apr. 21, 2020, which is a § 371 national stage of PCT International Application No. PCT/EP2015/062138, filed Jun. 1, 2015, claiming priority of Australian Patent Applications Nos. AU/2014/902257, filed Jun. 13, 2014, and AU/2014/902194, filed Jun. 10, 2014, the contents of each of which are hereby incorporated-by reference into the application.

This application is a continuation of U.S. application Ser. No. 16/828,121, filed Mar. 24, 2020, now allowed, which is a divisional of U.S. application Ser. No. 15/317,673, filed Dec. 9, 2016, which is a § 371 national stage of PCT International Application No. PCT/EP2015/062138, filed Jun. 1, 2015, claiming priority of Australian Patent Applications Nos. AU 2014902257, filed Jun. 13, 2014 and AU 2014902194, filed Jun. 10, 2014, the contents of each of which are hereby incorporated by reference into the application.

TECHNICAL FIELD

The present disclosure relates to stem cells which express high levels of Angeopoetin-1 (Ang1) and uses thereof in inhibiting TNF-alpha and/or IL-6 release and treating inflammatory disease such as diabetes.

BACKGROUND

Angiopoietin is part of a family of vascular growth factors that play a role in embryonic and postnatal angiogenesis. Ang1 promotes migration of endothelial and some non-endothelial cells such as smooth muscle cells. Ang1 also induces sprouting and reorganisation of endothelial cells into tubules. Ang1 exerts potent anti-inflammatory effects on endothelial cells, suppressing Vascular Endothelial Growth Factor (VEGF) induced upregulation of E-selectin, ICAM-1 and VCAM-1, and inhibiting leucocyte adhesion and trans-migration in response to VEGF and TNF-α (Kim et al. Circ Res., 89(6), 477-479, 2001).

The current therapy for most type-1 diabetic patients is based on regular subcutaneous injections of mixtures of short-acting and long-acting insulin preparations. Suspensions of soluble insulin particles of different size that give intermediate acting and long-acting components with more sustained action profiles are administered to achieve a constant basal level of the hormone (Heine et al. Br Med J (Clin Res Ed) 290:204-205, 1985).

A disadvantage of this current therapy is the delayed-action preparations do not generally produce smooth background levels of insulin, resulting in either hyperglycaemia or hypoglycaemia. Hyperglycaemia is problematic in that it can lead to further complications in diabetic patients. For example, chronic hyperglycaemia leads to severe microvascular (retinopathy and nephropathy), macrovascular (stroke, myocardial infarction), and neurological complications. These devastating complications can be prevented by normalization of blood glucose levels.

Stem cell-based technologies have emerged in recent years as a possible approach to treat diabetes. However, besides issues related to the underlying autoimmune disease, which may require lifelong immunosuppression, these technologies are yet to emerge as a viable therapeutic option.

Accordingly, there remains an unmet therapeutic need in patients with diabetes and/or its associated conditions or symptoms with new treatment options being required.

Citation or identification of any document in this application is not an admission that such document is available as prior art to the present disclosure.

SUMMARY

The present inventors have found that they are able to increase the production of anti-inflammatory cells in human subjects using genetically unmodified stem cells that express Ang1 at high levels without the need for transfection of the cells with a nucleic acid expressing Ang1.

The present inventors have also found that they are able to reduce TNF-alpha, reduce IL-6 and/or increase IL-10 levels in human subjects. These findings suggest that such genetically unmodified stem cells expressing elevated levels of Ang1 may be suitable for treating inflammatory disorders such as diabetes and associated conditions and symptoms thereof.

Indeed, the present inventors have found that they are able to reduce HbA1c, reduce fasting insulin levels and/or increase adiponectin levels in human subjects with diabetes using genetically unmodified stem cells that express Ang1 at high levels without the need for transfection of the cells with a nucleic acid expressing Ang1.

In other examples, the present inventors have also shown that they are able to improve symptoms of rheumatoid arthritis and diabetic nephropathy in human subjects with using genetically unmodified stem cells that express Ang1 at high levels without the need for transfection of the cells with a nucleic acid expressing Ang1.

Accordingly, in one example, the present disclosure provides a method of increasing production and/or function of anti-inflammatory cells in a subject in need thereof, the method comprising administering to the subject a composition comprising genetically unmodified stem cells wherein said genetically unmodified stem cells express angiopoietin-1 (Ang1) in an amount of at least 0.1 µg/$10^6$ cells.

In one example, the anti-inflammatory cells are Th2 cells, TReg cells or M2-type macrophages.

In another example, the method increases the number of M2-type macrophages in the subject.

In another example, the method increases the number of M2-type macrophages to at least 10% of the total monocyte population in the subject.

In another example, the method increases the number of M2-type macrophages to at least 20% of the total monocyte population in the subject.

In another example, the method increases the number of M2-type macrophages to at least 40% of the total monocyte population in the subject.

In another example, the method increases the number of M2-type macrophages to at least 80% of the total monocyte population in the subject.

In another example, the method increases the number of M2-type macrophages to at least 90% of the total monocyte population in the subject.

In another example, the M2-type macrophages are CD14+CD16+.

In another example, the M2-type macrophages are CD14+CD16+CD163+.

In another example, the M2-type macrophages are CD14+CD16+CD206+.

In another example, the M2-type macrophages are CD14+CD16+CD163+CD206+.

In another example, the M2-type macrophages are CD14++CD16+.

In another example, the M2-type macrophages are CD14++CD16+CD163+.

In another example, the M2-type macrophages are CD14++CD16+CD206+.

In another example, the M2-type macrophages are CD14++CD16+CD163+CD206+.

In another example, the method promotes the polarization of macrophages from an M1 to an M2 phenotype.

In another example, the method promotes the differentiation of pro-inflammatory T helper cells to Th2 or TReg cells.

In one example, the pro-inflammatory T helper cells are Th17 cells.

In an example, the increased production and/or function of anti-inflammatory cells in the subject results in:
a reduction in IL-6 level in the subject;
a reduction in TNF-alpha level in the subject; and/or,
an increase in IL-10 level in the subject.

In an example, the method increases the levels of anti-inflammatory cytokines in the subject.

In an example, the method increases the level of IL-10 in the subject.

In an example, the method decreases the levels of pro-inflammatory cytokines in the subject.

In an example, the method decreases the levels of any one of IL-6, TNF-alpha and/or IL-17 in the subject.

In an example, the method also inhibits the production and/or function of pro-inflammatory cells.

In an example, the pro-inflammatory cells are Th17 cells or M1-type macrophages.

In another example, the present disclosure provides a method wherein the method inhibits M1-type macrophage polarization.

In another example, the present disclosure provides a method wherein the method promotes the polarization of macrophages from an M1 to an M2 phenotype.

In another example, the present disclosure provides a method wherein the method inhibits M1-type macrophage derived cytokine release.

In another example, the present disclosure provides a method wherein the M1-type macrophage derived cytokines inhibited are TNF-alpha and/or IL-6.

In another example, the present disclosure provides a method of treating an inflammatory disease, the method comprising administering to the subject a composition comprising genetically unmodified stem cells wherein said genetically unmodified stem cells express angiopoietin-1 (Ang1) in an amount of at least 0.1 µg/$10^6$ cells.

In another example, the inflammatory disease is diabetes or an associated condition or symptom of diabetes selected from the group consisting of abnormal wound healing, symptoms of a heart attack, symptoms of a stroke, symptoms of peripheral vascular disease, amputation, symptoms of kidney disease, kidney failure, blindness, neuropathy, nephropathy, retinopathy, inflammation, impotence or non-alcoholic steatohepatitis (NASH).

For example, the present disclosure provides a method of treating rheumatoid arthritis.

For example, the present disclosure provides a method of treating diabetic retinopathy.

In another example, the method of the present disclosure comprises administering to the subject a composition comprising genetically unmodified stem cells wherein said genetically unmodified stem cells express angiopoietin-1 (Ang1) in an amount of at least 0.1 µg/$10^6$ cells. In another example, the stem cells express Ang1 in an amount of at least 0.5 µg/$10^6$ cells. In another example, the stem cells express Ang1 in an amount of at least 0.7 µg/$10^6$ cells. In another example, the stem cells express Ang1 in an amount of at least 1 µg/$10^6$ cells.

In another example, the stem cells express VEGF in an amount less than about 0.1 µg/$10^6$ cells. In another example, the stem cells express VEGF in an amount less than about 0.05 µg/$10^6$ cells. In another example, the stem cells express VEGF in an amount less than about 0.04 µg/$10^6$ cells. In another example, the stem cells express VEGF in an amount less than about 0.03 µg/$10^6$ cells. In another example, the stem cells express VEGF in an amount less than about 0.02 µg/$10^6$ cells. In another example, the stem cells express VEGF in an amount less than about 0.01 µg/$10^6$ cells.

In another example, the stem cells express Ang1:VEGF at a ratio of at least about 2:1. In another example, the stem cells express Ang1:VEGF at a ratio of at least about 10:1. In another example, the stem cells express Ang1:VEGF at a ratio of at least about 20:1. In another example, the stem cells express Ang1:VEGF at a ratio of at least about 30:1. In another example, the stem cells express Ang1:VEGF at a ratio of at least about 50:1.

In another example, the stem cells are mesenchymal stem cells. In another example, the stem cells are mesenchymal precursor cells. In another example, the stem cells are induced pluripotent stem cells (iPS cells).

In another example, the composition further comprising an acceptable pharmaceutical carrier.

In another example the composition is produced by culturing genetically unmodified stem cells according to the in-vitro methods described below.

In an example, the stem cells can be obtained from any mammal. For example, the stem cells may be derived from a primate, a cow, sheep, horse, dog, cat, or goat. In another example, the stem cell are human stem cells.

In another example, the inflammatory disease is type II diabetes.

In one example, the method of treating type II diabetes may comprise administering about 0.1×$10^6$ to about 3×$10^6$ stem cells per kg to the subject.

In one example, the method of treating type II diabetes may comprise administering about 0.3×$10^6$ to about 2×$10^6$ stem cells per kg to the subject.

In one example, the method of treating type II diabetes may comprise administering about 1×$10^6$ to about 2×$10^6$ stem cells per kg to the subject.

In one example, the method of treating type II diabetes may comprise administering about 2×$10^6$ stem cells per kg to the subject.

In one example, any one of the following indicates that the diabetes or associated condition or symptom of diabetes has been treated in the subject:
reduction in HbA1c value (% of total haemoglobin);
reduction in fasting insulin levels;
reduction in IL-6 levels;
reduction in TNF-α levels; and/or
increase in adiponectin levels In one example, the subjects has type II diabetes, wherein the subjects glucose levels are inadequately controlled.

In one example, the subjects glucose levels are inadequately controlled by metformin.

In one example, the subject has a baseline HbA1c value greater than 7.5%.

In one example, the subject has a baseline HbA1c value greater than or equal to 8%.

In one example, the inflammatory disease is rheumatoid arthritis.

In one example, the method of treating rheumatoid arthritis may comprise administering about $0.5 \times 10^6$ to about $3.0 \times 10^6$ stem cells per kg to the subject.

In one example, the method of treating rheumatoid arthritis may comprise administering about $1.0 \times 10^6$ to about $2.0 \times 10^6$ stem cells per kg to the subject.

In one example, any one of the following indicates that the rheumatoid arthritis has been treated:
ACR20;
ACR50
ACR70
reduction in IL-6 levels; and/or
reduction in disease activity score.

In another example, the inflammatory disease is diabetic neuropathy.

In one example, the method of treating rheumatoid arthritis may comprise administering about $1.0 \times 10^8$ to about $4.0 \times 10^8$ stem cells to the subject.

In one example, the method of treating rheumatoid arthritis may comprise administering about $1.5 \times 10^8$ to about $3.0 \times 10^8$ stem cells to the subject.

In one example, any one of the following indicates that the diabetic nephropathy has been treated:
inhibition of decline in eGFR and/or mGFR;
improvement in eGFR and/or mGFR; and/or
reduction in IL-6 levels.

In one example, the subjects baseline eGFR is greater than about 35 ml/min/1.73 $m^2$.

In one example, the subjects baseline eGFR is greater than 30 ml/min/1.73 $m^2$.

In one example, the subjects baseline eGFR is greater than 28 ml/min/1.73 $m^2$.

In one example, the subjects baseline eGFR is greater than 25 ml/min/1.73 $m^2$.

In one example, stem cells are administered systemically.

In one example, stem cells are administered intravenously.

In another example, the present disclosure relates to use of a composition comprising genetically unmodified stem cells wherein said genetically unmodified stem cells express elevated levels of angiopoietin-1 (Ang1) in the manufacture of a medicament for treating an inflammatory disease.

In another example, the present disclosure relates to a composition comprising genetically unmodified stem cells wherein said genetically unmodified stem cells express elevated levels of angiopoietin-1 (Ang1) for use in treating an inflammatory disease.

In another example, the present disclosure relates to a composition comprising genetically unmodified stem cells wherein said genetically unmodified stem cells express elevated levels of angiopoietin-1 (Ang1) when used for treating an inflammatory disease.

DETAILED DESCRIPTION

General Techniques and Definitions

Figure 1:
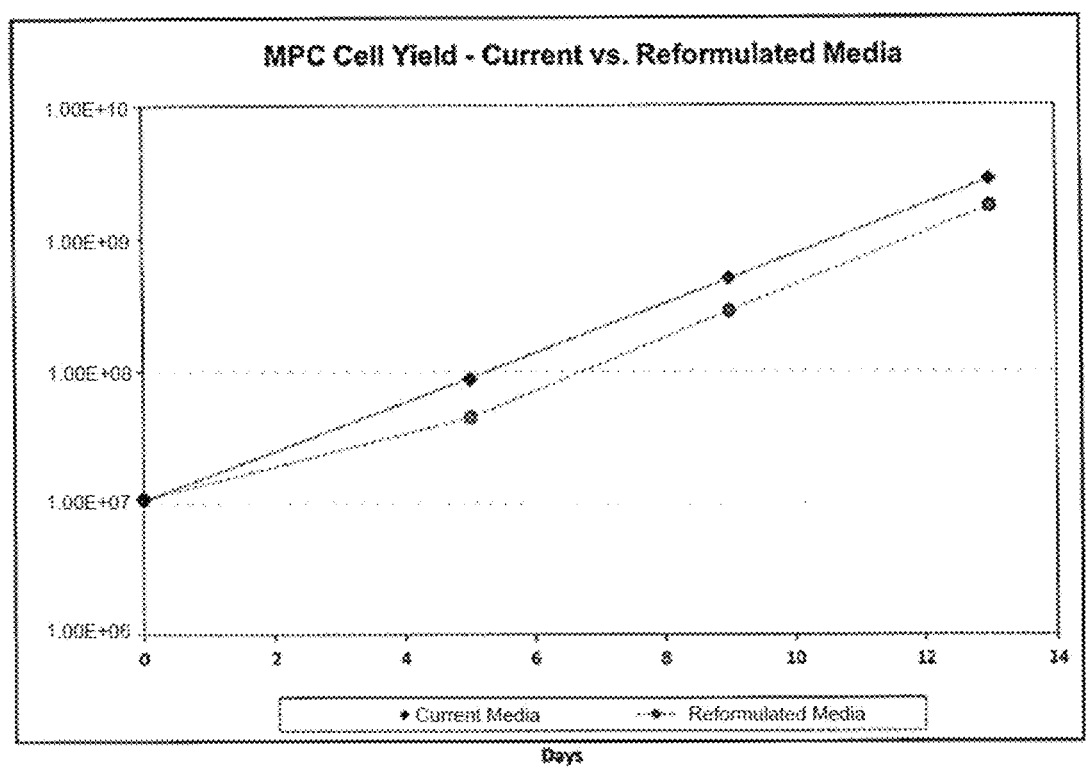
FIG. 1: MPC growth with current (process A) and reformulated culture media (process B). Y axis indicates cell numbers; X axis is time in days. Control media is the culture media used in process A and reformulated media is the culture media used in process B.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure, as described herein.

Any example disclosed herein shall be taken to apply mutatis mutandis to any other example unless specifically stated otherwise.

Unless specifically defined otherwise, all technical and scientific terms used herein shall be taken to have the same meaning as commonly understood by one of ordinary skill in the art (e.g., in cell culture, molecular genetics, stem cell differentiation, immunology, immunohistochemistry, protein chemistry, and biochemistry).

Unless otherwise indicated, the stem cells, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, more preferably +/−5%, of the designated value.

Volume percent (v/v %) defines [(volume of solute)/(volume of solution)]×100%. Volume percent is relative to the volume of solution. For example, cell culture media supplemented with 5% v/v FCS means there are about 5 ml FCS for every 100 ml of cell culture media.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Stem Cells

As used herein, the term "stem cell" refers to self-renewing cells that are capable of giving rise to phenotypically and genotypically identical daughters as well as at least one other final cell type (e.g., terminally differentiated cells). The term "stem cells" includes totipotential, pluripotential and multipotential cells, as well as progenitor and/or precursor cells derived from the differentiation thereof. The stem cell may be an adult or embryonic stem cell.

As used herein, the term "totipotent cell" or "totipotential cell" refers to a cell that is able to form a complete embryo (e.g., a blastocyst).

As used herein, the term "pluripotent cell" or "pluripotential cell" refers to a cell that has complete differentiation versatility, i.e., the capacity to grow into any of the mammalian body's approximately 260 cell types. A pluripotent cell can be self-renewing, and can remain dormant or quiescent within a tissue.

By "multipotential cell" or "multipotent cell" we mean a cell which is capable of giving rise to any of several mature cell types. As used herein, this phrase encompasses adult progenitor cells and multipotential progeny of these cells. Unlike a pluripotent cell, a multipotent cell does not have the capacity to form all of the cell types.

As used herein, the term "mesenchymal lineage precursor or stem cell" refers to cells that can differentiate into a mesenchymal cell type. For example, mesenchymal lineage precursor cells and mesenchymal precursor cells can differentiate into bone, cartilage, muscle and fat cells, and fibrous connective tissue.

In one example the stem cells expressing elevated levels of Ang1 are STRO-1+ mesenchymal precursor cells.

STRO-1+ multipotential cells are cells found in bone marrow, blood, dental pulp, adipose tissue, skin, spleen, pancreas, brain, kidney, liver, heart, retina, brain, hair follicles, intestine, lung, lymph node, thymus, bone, ligament, tendon, skeletal muscle, dermis, and periosteum. Thus, STRO-1+ multipotential cells are capable of differentiating into a large number of cell types including, but not limited to, adipose, osseous, cartilaginous, elastic and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. In one embodiment STRO-1+ multipotential cells are non-hematopoietic progenitor cells which divide to yield daughter cells that are either stem cells or are precursor cells which in time will irreversibly differentiate to yield a phenotypic cell.

In one example, STRO-1+ cells are enriched from a sample obtained from a subject, e.g., a subject to be treated or a related subject or an unrelated subject (whether of the same species or different). The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% or 85% or 95% or 99% STRO-1+ cells. In this regard, the term "population of cells enriched for STRO-1+ cells" will be taken to provide explicit support for the term "population of cells comprising X % STRO-1+ cells", wherein X % is a percentage as recited herein. The STRO-1+ cells can, in some examples, form clonogenic colonies, e.g. CFU-F (fibroblasts) or a subset thereof (e.g., 50% or 60% or 70% or 80% or 90% or 95%) can have this activity.

In one example, the stem cells expressing elevated levels of Ang1 are enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1+ does not mean that the cells are selected by STRO-1 expression. In one example, the cells are selected based on at least STRO-3 expression, e.g., they are STRO-3+ (TNAP+). In another example, the cells are selected based on at least STRO-4 expression, e.g., they are STRO-4+.

Reference to selection of a cell or population thereof does not necessarily require selection from a specific tissue source. As described herein STRO-1+ cells can be selected from or isolated from or enriched from a large variety of sources. That said, in some examples, these terms provide support for selection from any tissue comprising STRO-1+ cells (e.g., MPCs) or vascularized tissue or tissue comprising pericytes (e.g., STRO-1+ pericytes) or any one or more of the tissues recited herein.

In one example, the stem cells expressing elevated levels of Ang1 express one or more markers individually or collectively selected from the group consisting of STRO-1+, TNAP+, VCAM-1+, THY-1+, STRO-2+, STRO-4+(HSP-90β), CD45+, CD146+, 3G5+, CC9 or any combination thereof.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

In one example, STRO-1+ cells are STRO-1$^{bright}$ (syn. STRO-1$^{bri}$) In one example, the STRO-1$^{bri}$ cells are preferentially enriched relative to STRO-1$^{dim}$ or STRO-1$^{intermediate}$ cells.

In one example, STRO-1$^{bright}$ cells are additionally one or more of TNAP+, VCAM-1+, THY-1+, STRO-2+, STRO-4+(HSP-90R) and/or CD146+. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the STRO-1$^{bright}$ are isolated by immunoselection. In one example, STRO-1$^{bright}$ cells are isolated by immunoselection of cells expressing TNAP. As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

In one example, the mesenchymal precursor or stem cells are CD29+, CD54+, CD73+, CD90+, CD102+, CD105+, CD106+, CD166+, MHC1+ mesenchymal stem cells (e.g. remestemcel-L).

In one example, mesenchymal precursor cells are perivascular mesenchymal precursor cells as defined in WO 2004/85630. For example, the mesenchymal precursor cells express a marker of a perivascular cell, e.g., the cells are STRO-1+ or STRO-1b$^{right}$ and/or 3G5+. In one example, the cells are or were previously or are progeny of cells that were isolated from vascularized tissue or organs or parts thereof.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labelled or is undetectable above background levels, e.g., levels detected using an isotype control antibody.

The term "bright", when used herein, refers to a marker on a cell surface that generates a relatively high signal when detectably labelled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labelled with a FITC-conjugated STRO-1 antibody as determined by fluorescence activated cell sorting (FACS) analysis, than non-bright cells (STRO-1$^{dull/dim}$). In one example, "bright" cells constitute at least about 0.1% of the most brightly labelled bone marrow mononuclear cells contained in the starting sample. In other examples, "bright" cells constitute at least about 0.1%, at least about 0.5%, at least about 1%, at least about 1.5%, or at least about 2%, of the most brightly labelled bone marrow mononuclear cells contained in the starting sample. In an example, STRO-1$^{bright}$ cells have 2 log magnitude higher expression of STRO-1 surface expression relative to "background", namely cells that are STRO-1−. By comparison, STRO-1$^{dim}$ and/or STRO-1$^{intermediate}$ cells have less than 2 log magnitude higher expression of STRO-1 surface expression, typically about 1 log or less than "background".

In one example, a significant proportion of the STRO-1+ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another example, the STRO-1+ cells are not capable of giving rise, upon culturing, to hematopoietic cells.

In one example, the presently described stem cells are mesenchymal stem cells. The mesenchymal stem cells (MSC) may be a homogeneous composition or may be a mixed cell population enriched in MSCs. Homogeneous mesenchymal stem cell compositions may be obtained by culturing adherent marrow or periosteal cells, and the mesenchymal stem cells may be identified by specific cell surface markers which are identified with unique monoclonal antibodies. A method for obtaining a cell population enriched in mesenchymal stem cells is described, for example, in U.S. Pat. No. 5,486,359. Alternative sources for mesenchymal stem cells include, but are not limited to, blood, skin, cord blood, muscle, fat, bone, and perichondrium.

Recognition, selection and purification of stem cells carrying the cell surface markers described above can be effected by a number of different methods. For example, application of a binding agent to the marker concerned followed by a separation of those cells that exhibit binding, being either high level binding, or low level binding or no binding.

For example binding agents can include antibodies such as monoclonal antibodies or antibody based molecules.

Antibodies and other binding molecules can be used in various techniques to select and purify stem cells expressing the particular cell surface markers.

Techniques for selection and purification may include, but are not limited to, magnetic separation, using antibody-coated magnetic beads, affinity chromatography and "panning" with antibody attached to a solid matrix, fluorescence-activated cell sorting (FACS).

Stem cells expressing elevated levels of Ang1 expressing particular markers may be selected or purified from a cell population via positive immunoselection. For example, mesenchymal precursor cells can be isolated and enriched from a cell population based on the cell surface expression of the STRO-1 antibody (see for example Gronthos and Simmons 1995).

Isolated stem cells according to the present disclosure can be expanded in-vitro by culture. As will be appreciated by those skilled in the art, the stem cells can be cryopreserved, thawed and subsequently expanded in-vitro by culture. In one example, the stem cells are seeded in growth medium and allowed to adhere to the culture vessel overnight at 37° C., 20% $O_2$. The growth medium is subsequently replaced and the cells cultured for a further 68 to 72 hours at 37° C., 5% $O_2$.

In an example, isolated stem cells are seeded at 50,000 cells/cm$^2$ in serum supplemented growth medium and allowed to adhere to the culture vessel overnight at 37° C., 20% $O_2$. The growth medium is subsequently replaced with Chondrogenic Basal Medium (CBM; Lonza, Walkersville, MD) supplemented with 0.5% bovine serum albumin (BSA) and the cells cultured for a further 68 to 72 hours at 37° C., 5% $O_2$.

Various other methods of primary stem cell culture are known in the art. For example, primary stem cell culture can be carried out using the methods described in Gronthos and Simmons 1995.

The cultured stem cells are phenotypically different to cells in-vivo. They may express, for example, CD44.

In one embodiment the cultured stem cells are biologically different to cells in-vivo, having a higher rate of regeneration.

The cultured stem cells may be cryopreserved prior to administration to a subject. For example, stem cells expressing elevated levels of Ang1 are cryopreserved prior to administration to a subject.

Genetically-Unmodified Cells

As used herein, the term "genetically unmodified" refers to cells that have not been modified by transfection with a nucleic acid expressing or encoding Ang1. For the avoidance of doubt, in the context of the present disclosure a stem cell transfected with a nucleic acid encoding Ang1 would be considered genetically modified. In the context of the present disclosure the "genetically unmodified" cell naturally expresses Ang1 to some extent.

Expression of Ang1 and/or VEGF

The stem cells expressing elevated levels of Ang1 are genetically unmodified and express Ang1 in an amount of at least $0.1 \, \mu g/10^6$ cells. However, in various embodiments it is envisaged that the stem cells expressing elevated levels of Ang1 may express Ang1 in an amount of at least $0.2 \, \mu g/10^6$ cells, $0.3 \, \mu g/10^6$ cells, $0.4 \, \mu g/10^6$ cells, $0.5 \, \mu g/10^6$ cells, $0.6 \, \mu g/10^6$ cells, $0.7 \, \mu g/10^6$ cells, $0.8 \, \mu g/10^6$ cells, $0.9 \, \mu g/10^6$ cells, $1 \, \mu g/10^6$ cells, $1.1 \, \mu g/10^6$ cells, $1.2 \, \mu g/10^6$ cells, $1.3 \, \mu g/10^6$ cells, $1.4 \, \mu g/10^6$ cells, $1.5 \, \mu g/10^6$ cells.

In one example, stem cells expressing elevated levels of Ang1 express Ang1 in an amount of at least $0.2 \, \mu g/10^6$ cells to about $1.5 \, \mu g/10^6$ cells.

In one example, stem cells expressing elevated levels of Ang1 express Ang1 in an amount of at least $0.3 \, \mu g/10^6$ cells to about $1.4 \, \mu g/10^6$ cells.

In one example, stem cells expressing elevated levels of Ang1 express Ang1 in an amount of at least $0.4 \, \mu g/10^6$ cells to about $1.3 \, \mu g/10^6$ cells.

In one example, stem cells expressing elevated levels of Ang1 express Ang1 in an amount of at least $0.5 \, \mu g/10^6$ cells to about $1.2 \, \mu g/10^6$ cells.

In one example, stem cells expressing elevated levels of Ang1 express Ang1 in an amount of at least $0.55 \, \mu g/10^6$ cells to about $1.1 \, \mu g/10^6$ cells.

In one example, stem cells expressing elevated levels of Ang1 express Ang1 in an amount of at least $0.6 \, \mu g/10^6$ cells to about $1.0 \, \mu g/10^6$ cells.

In one example, stem cells expressing elevated levels of Ang1 express Ang1 in an amount of at least $0.65 \, \mu g/10^6$ cells to about $0.9 \, \mu g/10^6$ cells.

In one example, stem cells expressing elevated levels of Ang1 express Ang1 in an amount of at least $0.7 \, \mu g/10^6$ cells to about $0.8 \, \mu g/10^6$ cells.

In another aspect, the genetically unmodified stem cells expressing elevated levels of Ang1 express VEGF in an amount less than about $0.01 \, \mu g/10^6$ cells.

In another aspect, the genetically unmodified stem cells expressing elevated levels of Ang1 express VEGF in an amount less than about $0.05 \, \mu g/10^6$ cells. However, in various embodiments it is envisaged that the stem cells expressing elevated levels of Ang1 may express VEGF in an amount less than about $0.05 \, \mu g/10^6$ cells, $0.04 \, \mu g/10^6$ cells, $0.03 \, \mu g/10^6$ cells, $0.02 \, \mu g/10^6$ cells, $0.01 \, \mu g/10^6$ cells, $0.009 \, \mu g/10^6$ cells, $0.008 \, \mu g/10^6$ cells, $0.007 \, \mu g/10^6$ cells, $0.006 \, \mu g/10^6$ cells, $0.005 \, \mu g/10^6$ cells, $0.004 \, \mu g/10^6$ cells, $0.003 \, \mu g/10^6$ cells, $0.002 \, \mu g/10^6$ cells, $0.001 \, \mu g/10^6$ cells.

In one example, stem cells expressing elevated levels of Ang1 express VEGF in an amount of at least 0.001 µg/$10^6$ cells to about 0.1 µg/$10^6$ cells.

In one example, stem cells expressing elevated levels of Ang1 express VEGF in an amount of at least 0.0025 µg/$10^6$ cells to about 0.09 µg/$10^6$ cells.

In one example, stem cells expressing elevated levels of Ang1 express VEGF in an amount of at least 0.0075 µg/$10^6$ cells to about 0.08 µg/$10^6$ cells.

In one example, stem cells expressing elevated levels of Ang1 express VEGF in an amount of at least 0.01 µg/$10^6$ cells to about 0.07 µg/$10^6$ cells.

In one example, stem cells expressing elevated levels of Ang1 express VEGF in an amount of at least 0.02 µg/$10^6$ cells to about 0.06 µg/$10^6$ cells.

In one example, stem cells expressing elevated levels of Ang1 express VEGF in an amount of at least 0.02 µg/$10^6$ cells to about 0.05 µg/$10^6$ cells.

The amount of cellular Ang1 and/or VEGF that is expressed in a composition or culture of stem cells may be determined by methods known to those skilled in the art. Such methods include, but are not limited to, quantitative assays such as quantitative ELISA assays, for example. It is to be understood, however, that the scope of the present disclosure is not to be limited to any particular method for determining the amount or level of Ang1 or VEGF expressed in the stem cells expressing elevated levels of Ang1.

In one example the level of Ang1 or VEGF expressed by a composition or culture of stem cells is determined by an ELISA assay. In such an assay, a cell lysate from a culture of stem cells is added to a well of an ELISA plate. The well may be coated with a primary antibody, either a monoclonal or a polyclonal antibody(ies), against the Ang1 or VEGF. The well then is washed, and then contacted with a secondary antibody, either a monoclonal or a polyclonal antibody(ies), against the primary antibody. The secondary antibody is conjugated to an appropriate enzyme, such as horseradish peroxidase, for example. The well then may be incubated, and then is washed after the incubation period. The wells then are contacted with an appropriate substrate for the enzyme conjugated to the secondary antibody, such as one or more chromogens. Chromogens which may be employed include, but are not limited to, hydrogen peroxide and tetramethylbenzidine. After the substrate(s) is (are) added, the well is incubated for an appropriate period of time. Upon completion of the incubation, a "stop" solution is added to the well in order to stop the reaction of the enzyme with the substrate(s). The optical density (OD) of the sample then is measured. The optical density of the sample is correlated to the optical densities of samples containing known amounts of Ang1 or VEGF in order to determine the amount of Ang1 or VEGF expressed by the culture of stem cells being tested.

In another aspect, the genetically unmodified stem cells expressing elevated levels of Ang1 express Ang1:VEGF at a ratio of at least about 2:1. However, in various embodiments it is envisaged that the stem cells expressing elevated levels of Ang1 may express Ang1:VEGF at a ratio of at least about 10:1, 15:1, 20:1, 21:1, 22:1, 23:1, 24:1, 25:1, 26:1, 27:1, 28:1, 29:1, 30:1, 31:1, 32:1, 33:1, 34:1, 35:1, 50:1.

Methods for determining the Ang1:VEGF expression ratio will be apparent to one of skill in the art. In an example of a method of determining a ratio of Ang 1 and VEGF expression, Ang1 and VEGF expression levels are quantitated via quantitative ELISA as discussed above. In such an example, after quantifying the levels of Ang1 and VEGF, a ratio based on the quantitated levels of Ang1 and VEGF could be represented as: (level of Ang1/level of VEGF)= Ang1:VEGF ratio.

Cellular Compositions

In one example of the present disclosure stem cells are administered in the form of a composition. In one example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay metabolic syndrome and/or obesity.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

Stem cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. J. Ped. Surg. 23:3-9 1988; Cima, et al. Biotechnol. Bioeng. 38:145 1991; Vacanti, et al. Plast. Reconstr. Surg. 88:753-9 1991; or synthetic polymers such as polyanhydrides, polyorthoesters, and polylactic acid.

In another example, the cells may be administered in a gel scaffold (such as Gelfoam from Upjohn Company.

The cellular compositions described herein may be administered alone or as admixtures with other cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of cells. For example, the composition comprises about $1\times10^5$ stem cells with elevated Ang1 levels to about $1\times10^7$ stem cells with elevated Ang1 levels or about $1\times10^6$ stem cells with elevated Ang1 to about $5\times10^6$ stem cells with elevated Ang1 per kg.

The exact dosage of stem cells to be administered is dependent upon a variety of factors, including, but not limited to, the age, weight, and sex of the patient, the disease(s) or disorder(s) being treated, and the extent and severity thereof.

In one example, a low dose of cells is administered to the subject. Exemplary dosages include between about $0.1\times10^4$ to about $0.5\times10^6$ cells per kg, for example, between about $0.1\times10^5$ to about $0.5\times10^6$ cells per kg, such as, between about $0.5\times10^5$ to about $0.5\times10^6$ cells per kg, for example, between about $0.1\times10^6$ to about $0.5\times10^6$ cells per kg, e.g., about $0.2\times10^6$ or $0.3\times10^6$ or $0.4\times10^6$ cells per kg.

For example, about $0.1\times10^6$, about $0.2\times10^6$, about $0.3\times10^6$, about $0.4\times10^6$, about $0.5\times10^6$ cells per kg can be administered to the subject.

In other examples, about $0.6\times10^6$, about $0.7\times10^6$, about $0.8\times10^6$, about $0.9\times10^6$, about $1.0\times10^6$ about $1.1\times10^6$, about $1.2\times10^6$, about $1.3\times10^6$, about $1.4\times10^6$ cells per kg are administered to the subject.

In one example, a high dose of cells is administered to the subject. Exemplary dosages include at least about $1.5\times10^6$ cells/kg. For example, a high dose comprises between about $1.5\times10^6$ to about $6\times10^6$ cells/kg, such as between about $1.5\times10^6$ to about $5\times10^6$ cells/kg, for example, between about $1.5\times10^6$ to about $4\times10^6$ cells/kg, for example, between about $1.5\times10^6$ to about $3\times10^6$ cells/kg. For example, a high dose comprises about $1.5\times10^6$ or about $2\times10^6$ cells/kg. For example, a high dose comprises about $1.5\times10^6$ cells/kg. For example, a high dose comprises about $2\times10^6$ cells/kg. For example, a high dose comprises about $3\times10^6$ cells/kg.

In other examples, about $1.5\times10^6$, about $1.6\times10^6$, about $1.7\times10^6$, about $1.8\times10^6$, about $1.9\times10^6$, about $2.0\times10^6$, about $2.1\times10^6$, about $2.2\times10^6$, about $2.3\times10^6$, about $2.4\times10^6$, about $2.5\times10^6$, about $2.6\times10^6$, about $2.7\times10^6$, about $2.8\times10^6$, about $2.9\times10^6$, about $3.0\times10^6$, about $3.1\times10^6$, about $3.2\times10^6$, about $3.3\times10^6$, about $3.4\times10^6$, about $3.5\times10^6$, about $3.6\times10^6$, about $3.7\times10^6$, about $3.8\times10^6$, about $3.9\times10^6$, about $4.0\times10^6$ cells per kg are administered to the subject.

In other examples, about $1.0\times10^8$, about $1.1\times10^8$, about $1.2\times10^8$, about $1.3\times10^8$, about $1.4\times10^8$, about $1.5\times10^8$, about $1.6\times10^8$, about $1.7\times10^8$, about $1.8\times10^8$, about $1.9\times10^8$, about $2.0\times10^8$, about $2.1\times10^8$, about $2.2\times10^8$, about $2.3\times10^8$, about $2.4\times10^8$, about $2.5\times10^8$, about $2.6\times10^8$, about $2.7\times10^8$, about $2.8\times10^8$, about $2.9\times10^8$ cells, about $3.0\times10^8$, about $3.1\times10^8$, about $3.2\times10^8$, about $3.3\times10^8$, about $3.4\times10^8$, about $3.5\times10^8$, about $3.6\times10^8$, about $3.7\times10^8$, about $3.8\times10^8$, about $3.9\times10^8$, about $4.0\times10^8$ cells are administered to the subject.

The mesenchymal lineage precursor or stem cells can comprise at least about 5% of the cell population of the composition. In other examples, the mesenchymal lineage precursor or stem cells can comprise at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% of the cell population of the composition.

Stem cells that express CD44 can comprise at least about 5% of the cell population of the composition. In other examples, stem cells that express CD44 can comprise at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 100% of the cell population of the composition.

In some examples, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors.

The stem cells may be administered systemically, such as, for example, by intravenous, intraarterial, or intraperitoneal administration.

The mesenchymal lineage precursor or stem cells may also be administered by intranasal, intramuscular, intraarticular or intracardiac administration.

For example, the mesenchymal lineage precursor or stem cells can be administered directly into sore or swollen joint.

In another example, stem cells expressing elevated levels of Ang1 are administered via intracoronary infusion. For example, mesenchymal lineage precursor or stem cells may be administered into the left anterior descending (LAD) artery.

In another example, stem cells expressing elevated levels of Ang1 are administered via intrarenal infusion.

In an example, stem cells expressing elevated levels of Ang1 may be administered as a single dose.

In some examples, stem cells expressing elevated levels of Ang1 may be administered over multiple doses. For example, at least 2, at least 3, at least 4, at least 5, at least 6, at least 7, at least 8, at least 9, at least 10 doses.

The composition comprising stem cells expressing elevated levels of Ang1 may be cryopreserved. Cryopreservation of stem cells can be carried out using slow-rate cooling methods or 'fast' freezing protocols known in the art. In an example, the method of cryopreservation maintains similar phenotypes, cell surface markers and growth rates of cryopreserved cells in comparison with unfrozen cells.

The cryopreserved composition may comprise a cryopreservation solution. The pH of the cryopreservation solution is typically about 6.5 to 8.

In an example the pH of the cryopreservation solution is about 7.4.

The cyropreservation solution may comprise a sterile, non-pyrogenic isotonic solution such as, for example, PlasmaLyte A®. 100 mL of PlasmaLyte A® contains 526 mg of sodium chloride, USP (NaCl); 502 mg of sodium gluconate ($C_6H_{11}NaO_7$); 368 mg of sodium acetate trihydrate, USP ($C_2H_3NaO_2$ $3H_2O$); 37 mg of potassium chloride, USP (KCl); and 30 mg of magnesium chloride, USP ($MgCl_2$ 6H$_2$O). It contains no antimicrobial agents. The pH is adjusted with sodium hydroxide. The pH is 7.4 (6.5 to 8.0).

To facilitate freezing, a cryoprotectant such as, for example, dimethylsulfoxide (DMSO), is usually added to the cryopreservation solution. Ideally, the cryoprotectant should be nontoxic for cells and patients, nonantigenic, chemically inert, provide high survival rate after thawing and allow transplantation without washing. However, the most commonly used cryoprotector, DMSO, shows some cytotoxicity. Hydroxylethyl starch (HES) may be used as a substitute or in combination with DMSO to reduce cytotoxicity of the cryopreservation solution.

The cryopreservation solution may comprise one or more of DMSO, hydroxyethyl starch, human serum components and other protein bulking agents. In one example, the cryopreserved solution comprises about 5% human serum albumin (HSA) and about 10% DMSO. The cryopreservation solution may further comprise one or more of methylcellulose, polyvinyl pyrrolidone (PVP) and trehalose.

The cryopreserved composition may be thawed and administered directly to the subject. Alternatively, the cryopreserved composition may be thawed and the mesenchymal lineage precursor or stem cells resuspended in an alternate solution prior to administration.

Stem cells expressing elevated levels of Ang1 are administered to an animal in an amount effective to treat a disease or disorder in the animal. The animal may be a mammal, and the mammal may be a primate, including human and non-human primates.

In an example, stem cells expressing elevated levels of Ang1 are administered to a human.

In an example, stem cells expressing elevated levels of Ang1 are administered to a human.

In an example, stem cells expressing elevated levels of Ang1 are administered to a subject with diabetes.

In an example, stem cells expressing elevated levels of Ang1 are administered to a subject with type II diabetes.

In an example, stem cells expressing elevated levels of Ang1 are administered to a subject with type II diabetes with baseline HbA1c values greater than about 7%. For example, stem cells expressing elevated levels of Ang1 can be administered to a subject with type II diabetes with baseline HbA1c values greater than about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%.

In an example, stem cells expressing elevated levels of Ang1 can be administered to a subject with type II diabetes with baseline HbA1c values greater than or equal to about 8.0%.

Methods for determining HbA1c value (% of total haemoglobin) will be apparent to one of skill in the art. Examples of methods used for determining HbA1c value (% of total haemoglobin) include high-performance liquid chromatography (HPLC) or immunoassay. One of skill in the art would also be aware that HbA1c value can be represented as other values, for example, as mmol/mol.

In an example, subjects HbA1c values are determined by HPLC.

In an example, subjects HbA1c values are determined by immunoassay.

In an example, stem cells expressing elevated levels of Ang1 are administered to a subject with type II diabetes, wherein the subjects glucose levels are inadequately controlled.

In an example, stem cells expressing elevated levels of Ang1 are administered to a subject with type II diabetes, wherein the subjects glucose levels are inadequately controlled by metformin or metformin plus one other oral therapeutic agent.

In an example, stem cells expressing elevated levels of Ang1 are administered to a subject with chronic kidney disease.

In an example, stem cells expressing elevated levels of Ang1 are administered to a subject with diabetic nephropathy.

In an example, stem cells expressing elevated levels of Ang1 are administered to a subject with type II diabetes and chronic kidney disease.

In an example, stem cells expressing elevated levels of Ang1 are administered to a subject with type II diabetes and diabetic nephropathy.

The estimated glomerular filtration rate (eGFR) is used to screen for and detect early kidney damage and to monitor kidney status.

In an example, stem cells expressing elevated levels of Ang1 are administered to a subject with baseline eGFR greater than about 35 ml/min/1.73 m$^2$, about 34 ml/min/1.73 m$^2$, about 44 ml/min/1.73 m$^2$, about 32 ml/min/1.73 m$^2$, about 31 ml/min/1.73 m$^2$, about 30 ml/min/1.73 m$^2$, about 29 ml/min/1.73 m$^2$, about 28 ml/min/1.73 m$^2$, about 27 ml/min/1.73 m$^2$, about 26 ml/min/1.73 m$^2$, about 25 ml/min/1.73 m$^2$.

In an example, stem cells expressing elevated levels of Ang1 are administered to a subject with kidney function stage 3A, 3B, 4 or 5.

In an example, stem cells expressing elevated levels of Ang1 are administered to a subject with kidney function stage 3B.

In an example, stem cells expressing elevated levels of Ang1 are administered to a subject with In an example, stem cells expressing elevated levels of Ang1 are administered to a subject with baseline eGFR greater than or equal to 30 ml/min/1.73 m$^2$ Methods for estimating GFR will be apparent to one of skill in the art and are exemplified below. eGFR may be calculated using creatinine and/or cystatin C levels.

For example, eGFR may be calculated using the MDRD equation:

$$\text{GFR}(\text{mL/min}/1.73\text{ m}^2) = 175 \times (S_{cr})^{-1.154} \times (\text{Age})^{-0.203} \times (0.742 \text{ if female}) \times (1.212 \text{ if African American}).$$

In other example, eGFR may be calculated using the CKD-EPI equation (Levey et al. Ann Intern. Med. 150(9), 604-12, 2009):

$$\text{GFR} = 141 \times \min(S_{cr}/\kappa, 1)^\alpha \times \max(S_{cr}/\kappa, 1)^{-1.209} \times 0.993^{\text{Age}} \times 1.018[\text{if female}] \times 1.159[\text{if black}]$$

where:

$S_{cr}$ is serum creatinine in mg/dL,

K is 0.7 for females and 0.9 for males,

α is −0.329 for females and −0.411 for males, min indicates the minimum of $S_{cr}/K$ or 1, and max indicates the maximum of $S_{cr}/K$ or 1.

eGFR may also continually calculated and monitored over time to determine whether eGFR is declining or improving. eGFR can be compared between control and treatment groups to identify whether decline in eGFR is inhibited in treatment groups.

In an example, stem cells expressing elevated levels of Ang1 are administered to a subject with arthritis.

In an example, stem cells expressing elevated levels of Ang1 are administered to a subject with rheumatoid arthritis.

In an example, stem cells expressing elevated levels of Ang1 are administered to a subject with rheumatoid arthritis classified as incomplete anti-TNFα responders.

In an example, stem cells expressing elevated levels of Ang1 are administered to a subject with rheumatoid arthritis who had failed a biologic therapy for rheumatoid arthritis.

In an example, stem cells expressing elevated levels of Ang1 are administered to a subject with rheumatoid arthritis who had failed two biologic therapies for rheumatoid arthritis.

In an example, stem cells expressing elevated levels of Ang1 are administered to a subject with rheumatoid arthritis who had failed three biologic therapies for rheumatoid arthritis.

Inhibition of TNF-Alpha, IL-6, IL-17

TNF-alpha, IL-6 and IL-17 are chemical messengers known as cytokines. These molecules are released from cells in response to various signals. In the context of the present invention, the term 'inhibit' or 'inhibiting' refers to the reduction or suppression of the measurable level of a substance such as a protein (e.g. a cytokine) or a process (e.g. cell differentiation or cell polarisation).

Accordingly, in an example, it is envisaged that administration of the cell composition comprising stem cells expressing elevated levels of Ang1 will reduce the measurable level of TNF-alpha, IL-17 and/or IL-6 in the subject. In this example, TNF-alpha, IL-17 and/or IL-6 release from cells is inhibited.

In one example, the present disclosure relates to a method of monitoring a subjects response to administration of stem cells expressing elevated levels of Ang1. In this example the levels or pro and/or anti-inflamatory markers such as cytokines may monitored over a period of time following administration of stem cells expressing elevated levels of Ang1.

In an example, the present disclosure relates to a method of monitoring a subjects response following administration of stem cells expressing elevated levels of Ang1, the method comprising, assessing the levels of inflammatory and/or anti-inflammatory markers in a sample such as a whole blood sample obtained from a subject that has been administered stem cells expressing elevated levels of Ang1 and determining whether the subject has responded to the administration of stem cells expressing elevated levels of Ang1 based on the levels of the pro and/or anti-inflammatory markers.

In an example, an increase in the level of anti-inflammatory and/or a decrease in inflammatory markers indicates that the subject has responded to the administration of stem cells.

In an example, the inflammatory and/or anti-inflammatory markers are cells or cell populations.

In an example, an increase in the number of anti-inflammatory cells and/or a decrease in the number of inflammatory cells indicates that the subject has responded to the administration of stem cells.

In an example, the anti-inflammatory cells are Th2 cells, Treg cells and/or M2-type macrophages.

In an example, the inflammatory cells are Th17 cells and/or M1-type macrophages.

Various assays are available to those skilled in the art which can be used to determine whether the number of inflammatory cells have been reduced and/or the number of anti-inflammatory cells have been increased.

For example, cell populations isolated from a whole blood sample can be assessed for expression of cell surface markers using flow cytometry based techniques such as fluorescence-activated cell sorting (FACS).

In one example, CD14+ monocytes can be purified from a whole blood sample obtained from a subject administered stem cells expressing elevated levels of Ang1. Monocytes can be assessed for CD16, CD163 and CD206 expression to identify the proportion of M1 and M2-type macrophages. Multiple samples can be assessed over time to determine whether M1-type macrophage numbers are decreased or decreasing and/or M2-type macrophage levels are increased or increasing. In an example, M1 and/or M2-type macrophage numbers are assessed relative to M1 and/or M2-type macrophage numbers in a sample obtained from the subject prior to administration of stem cells (e.g. a baseline or pre-treatment reference sample).

In another example, the inflammatory and/or anti-inflammatory markers assessed are cytokines.

In an example, the inflammatory markers are TNF-alpha, IL-17 and/or IL-6.

In an example, the anti-inflammatory marker is IL-10.

Various assays are available to those skilled in the art which can determine whether the TNF-alpha, IL-17 and/or IL-6 levels have been reduced or IL-10 levels have been increased. In one example, TNF-alpha, IL-17, IL-10 and/or IL-6 concentration levels can be determined using spectrophotometric techniques such as an Immulite chemiluminescent immunometric assay. In another example, TNF-alpha, IL-17, IL-10 and/or IL-6 concentration levels can be measured using the Luminex platform, using commercially available kits (Millipore).

In an example, administration of the cell composition comprising stem cells expressing elevated levels of Ang1 will inhibit the release of TNF-alpha and/or IL-6 by macrophages. Various methods are available to those skilled in the art which can determine whether TNF-alpha and/or IL-6 release from macrophages is reduced. For example, macrophages could be cultured in-vitro and either exposed to a composition comprising stem cells expressing elevated levels of Ang1 or a suitable control. After a period of time, TNF-alpha and/or IL-6 release could then be assessed using the above exemplified methods. TNF-alpha and/or IL-6 levels in cells exposed to the cell composition comprising stem cells expressing elevated levels of Ang1 could then be compared to TNF-alpha and/or IL-6 levels in control cells to determine whether TNF-alpha and/or IL-6 levels are reduced.

Two distinct states of polarisation for macrophages have been defined: the classically activated (M1) macrophage phenotype or "M1-type macrophage" and the alternatively activated (M2) macrophage phenotype or M2-type macrophage" (Gordon and Taylor., Nat. Rev. Immunol. 5: 953-964, 2005; Mantovani et al., Trends Immunol. 23: 549-555, 2002). The M1-type macrophage has a "pro-inflammatory" cytokine profile (e.g. TNF-alpha, IL-6, IL-1-beta, IL-12, IL-23). Whereas, the M2-type macrophage has an "anti-inflammatory" cytokine profile (e.g. IL-10). In an example, it is envisaged that administration of the cell composition comprising stem cells expressing elevated levels of Ang1 will inhibit the release of cytokines by M1-type macrophages. In another example, it is envisaged that administration of the cell composition comprising stem cells expressing elevated levels of Ang1 will inhibit the release of TNF-alpha and/or IL-6 by M1-type macrophages. Various assays are available to those skilled in the art which can determine whether TNF-alpha, IL-6 and/or other cytokine release by M1-type macrophages is reduced. For example, using M1-type macrophages in the above described in-vitro assays. In this example, CD14+ monocytes could be purified by immunoselection from a whole blood sample.

Increasing Anti-Inflammatory Cell Production and/or Function

In one example, the present disclosure relates to a method of increasing the production and/or function of anti-inflammatory cells in a subject by administering stem cells expressing elevated levels of Ang1.

The term "anti-inflammatory cells" is used in the context of the present disclosure to refer to cells that illicit or mediate an anti-inflammatory response in a subject. "Anti-inflammatory cells" may act directly on a cell population or target to direct an anti-inflammatory response. Alternatively, anti-inflammatory cells encompassed by the present disclosure may express or secrete factors such as cytokines that act on specific a cell population or target to direct an anti-inflammatory response.

Examples of anti-inflammatory cells include Th2 cells, Treg cells and M2-type macrophages.

In one example, the present disclosure relates to a method of increasing the number of Th2 cells, Treg and/or M2-type macrophages in a subject by administering stem cells expressing elevated levels of Ang1.

In one example, the present disclosure relates to a method of increasing the number of M2-type macrophages in a subject by administering stem cells expressing elevated levels of Ang1.

In one example, the method of the present disclosure increases the number of M2-type macrophages to at least about 6%, at least about 7%, at least about 8%, at least about 9% of the total monocyte population in a subject.

In one example, the method of the present disclosure increases the number of M2-type macrophages to at least about 10% of the total monocyte population in a subject.

In one example, the method of the present disclosure increases the number of M2-type macrophages to at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% of the total monocyte population in the subject.

One of skill in the art could readily identify the % of M2-macropaages relative to a subjects total monocyte population using various methods known in the art. For example, M2-macrophages could be identified based on their expression of CD14 and CD16 as well as other markers such as CD163 and CD206.

In this example, a whole blood sample could be obtained from a subject, cells could be immunoselected via FACS based on their expression of CD14. CD14+ cells could then be assessed for expression of CD16, CD163 and CD206. The proportion of CD14+CD16+CD163+CD206+ could be calculated relative to the total CD14+ cell population in the sample.

In one example, the increased production and/or function of anti-inflammatory cells in the subject results in:
a reduction in IL-6 level in the subject;
a reduction in TNF-alpha level in the subject; and/or,
an increase in IL-10 level in the subject.

In another example, the methods of the present disclosure ma method of promoting the polarization of macrophages from an M1 to an M2 phenotype.

For example, the present disclosure provides a method of promoting the polarisation of an M1-type macrophage to a M2-type macrophage in a subject in need thereof, the method comprising administering to the subject a composition comprising genetically unmodified stem cells wherein said genetically unmodified stem cells express angiopoietin-1 (Ang1) in an amount of at least 0.1 µg/$10^6$ cells.

In this example, an increase in the production or number of CD14+CD16+ cells, CD14++CD16+ cells, CD14+CD16+CD163+ cells, CD14++CD16+CD163+ cells, CD14+CD16+CD206+ cells, CD14++CD16+CD206+ cells, CD14+CD16+CD163+CD206+ cells, CD14++CD16+CD163+CD206+ cells, CD14+CD163+ cells, CD14++CD163+ cells, CD14+CD206+ cells, CD14++CD206+ cells, CD14+CD163+206+ cells, CD14++CD163+CD206+ cells, reduction in IL-6 levels, reduction in TNF-alpha levels and/or an increase in IL-10 levels can indicate that polarisation of M1-type macrophages to M2-type macrophages has been promoted.

Conversely, in another example, the present disclosure provides a method of inhibiting the polarisation of an M2-type macrophage to an M1-type macrophage.

In another example, the present disclosure provides a method of inhibiting M1-type macrophage production and/or function in a subject in need thereof, the method comprising administering to the subject a composition comprising genetically unmodified stem cells wherein said genetically unmodified stem cells express elevated levels of angiopoietin-1 (Ang1).

Method of Treatment

The present disclosure relates to a method of treating an inflammatory disease.

As used herein, the term, "inflammatory disease" should be taken to encompass diseases including but not limited to, pruritus, skin inflammation, psoriasis, multiple sclerosis, rheumatoid arthritis, osteoarthritis, systemic lupus erythematosus, Hashimoto's thyroidis, myasthenia gravis, diabetes type I or II, diabetic nephropathy, asthma, inflammatory lung injury, inflammatory liver injury, inflammatory glomerular injury, atopic dermatitis, allergic contact dermatitis, irritant contact dermatitis, seborrhoeic dermatitis, Sjoegren's syndrome, keratoconjunctivitis, uveitis, inflammatory bowel disease, Crohn's disease, ulcerative colitis, an inflammatory disease of the joints, skin, or muscle, acute or chronic idiopathic inflammatory arthritis, myositis, a demyelinating disease, chronic obstructive pulmonary disease, interstitial lung disease, interstitial nephritis and chronic active hepatitis.

In an example, the inflammatory disease treated by the method of the present disclosure is diabetes. In another example, the inflammatory disease is an associated condition or symptom of diabetes. In this example, the symptoms which may be treated include abnormal wound healing, symptoms related to having a heart attack, such as chest pain, symptoms related to having a stroke, peripheral vascular disease, amputation, kidney disease, kidney failure, blindness, neuropathy, inflammation, impotence or nonalcoholic steatohepatitis (NASH).

For example, the inflammatory disease treated by the method of the present disclosure is rheumatoid arthritis.

For example, the inflammatory disease treated by the method of the present disclosure is diabetic retinopathy.

In an example, the present disclosure relates to a method of treating diabetes.

In an example, the present disclosure relates to a method of treating type II diabetes.

In an example, the present disclosure relates to a method of treating diabetic nephropathy.

In an example, the present disclosure relates to a method of treating rheumatoid arthritis.

As used herein, the term "treat" or "treatment" or "treating" shall be understood to mean administering a therapeutically effective amount of cells. In the context of the present disclosure, the term "therapeutically effective amount of cells" refers to an amount of cells, that is effective for preventing, ameliorating or treating an inflammatory disease or disorder. Such an effective amount will generally result in an improvement in the signs, symptoms and/or other indicators of an inflammatory disease or disorder. For example, in diabetes, an effective amount of cells can result in a reduction in HbA1c value, a reduction in cytokine levels such as IL-6 and/or TNF-α, a reduction in fasting insulin and/or an increase in adiponectin levels.

For example, in rheumatoid arthritis, an effective amount of cells can result in achievement of ACR20, ACR 50 and/or ACR70, a reduction in cytokine levels such as IL-6 and/or reduction in disease activity score.

For example, in diabetic nephropathy, an effective amount of cells can result in inhibition of decline in eGFR or mGFR, improvement in eGFR or mGFR and/or a reduction in cytokine levels such as IL-6.

In the context of diabetes or an associated condition or symptom thereof, various routine clinical assays are available to those skilled in the art which can be used to determine a reduction in HbA1c value, a reduction in fasting insulin and/or an increase in adiponectin levels. For example, a blood sample would generally be obtained from a subject and then subject to immunoassays to detect HbA1c, insulin and adiponectin levels.

Cell Culture Method

In an embodiment, a method of producing stem cells expressing elevated levels of Ang1 comprises culturing a population of stem cells in a cell culture media, wherein the cell culture media contains a short acting L-ascorbic acid derivative but does not contain a substantial amount of a long acting L-ascorbic acid derivative; and/or is supplemented with less than 10% v/v fetal calf serum.

The term "media" or "medium" as used in reference to cell culture, includes the components of the environment surrounding the cells. It is envisaged that the media contributes to and/or provides the conditions sufficient to induce expression of Ang1 expression. Media may be solid, liquid, gaseous or a mixture of phases and materials. Media can include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells.

The culture media used in methods of producing stem cells expressing elevated levels of Ang1 can be prepared by using a culture media used for culturing of stem cells as a basal culture media. The basal culture media includes, for example, Eagles minimal essential (MEM) culture media, alpha modified MEM culture media, and mixed culture media thereof, and is not particularly restricted providing it can be used for culturing of stem cells.

Further, the culture media can contain components such as fatty acids or lipids, vitamins, growth factors, cytokines, antioxidants, buffering agents, inorganic salts and the like.

The cell culture media can also contain all essential amino acids and may also contain non-essential amino acids. In general, amino acids are classified into essential amino acids (Thr, Met, Val, Leu, Ile, Phe, Trp, Lys, His) and non-essential amino acids (Gly, Ala, Ser, Cys, Gln, Asn, Asp, Tyr, Arg, Pro).

Ascorbic acid is an essential supplement for the growth and differentiation of various kinds of cells in culture. It is now understood that particular ascorbic acid derivatives are "short acting" because they are not stable in solution, especially under the normal cell culture conditions of neutral pH and 37° C. These short acting derivatives rapidly oxidise into oxalic acid or threonic acid. In culture media (pH 7) at 37° C., oxidation decreases the level of these short acting ascorbic acid derivatives by approximately 80-90% in 24 hours. Accordingly, short acting ascorbic acid derivatives have been replaced with more stable "long acting" ascorbic acid derivatives in conventional cell culture of various cell types.

In the context of the present disclosure the term "short acting" encompasses ascorbic acid derivatives that are oxidised by approximately 80-90% following 24 hours of cell culture under culture conditions of neutral pH and 37° C. In one example, the short acting L-ascorbic acid derivative is a L-ascorbic acid salt. For example, in the context of the present disclosure, L-ascorbic acid sodium salt is a "short acting" ascorbic acid derivative.

In contrast, the term "long acting" encompasses ascorbic acid derivatives that are not oxidised by approximately 80-90% following 24 hours of cell culture under culture conditions of neutral pH and 37° C. In one example, in the context of the present disclosure, L-ascorbic acid-2-phosphate is a "long acting" ascorbic acid derivative. Other examples of long acting ascorbic acid derivatives include Tetrahexyldecyl Ascorbate Magnesium Ascorbyl Phosphate and 2-O-α-D-Glucopyranosyl-L-ascorbic acid.

In an example, the cell culture media used in methods of producing stem cells expressing elevated levels of Ang1 is supplemented with a short acting ascorbic acid derivative. For example, the cell culture media may contain at least about 0.005 g/L of a short acting ascorbic acid derivative. In another example, the cell culture media may contain at least about 0.01 g/L of a short acting ascorbic acid derivative. For example, the cell culture media may contain at least about 0.02 g/L of a short acting ascorbic acid derivative. In another example, the cell culture media may contain at least about 0.03 g/L of a short acting ascorbic acid derivative. For example, the cell culture media may contain at least about 0.04 g/L of a short acting ascorbic acid derivative. In another example, the cell culture media may contain at least about 0.05 g/L of a short acting ascorbic acid derivative. In another example, the cell culture media may contain at least about 0.06 g/L of a short acting ascorbic acid derivative. In one example of this embodiment, the cell culture media is supplemented with sodium salt of L-ascorbate.

In another example, the cell culture media contains a short acting ascorbic acid derivative but does not contain a substantial amount of a long acting ascorbic acid derivative. For example, the cell culture media may contain a short acting ascorbic acid derivative but not more than 0.04 g/L of a long acting ascorbic acid derivative. In another example, the cell culture media may contain a short acting ascorbic acid derivative but not more than 0.03 g/L of a long acting ascorbic acid derivative. In another example, the cell culture media may contain a short acting ascorbic acid derivative but not more than 0.02 g/L of a long acting ascorbic acid derivative. In another example, the cell culture media may contain a short acting ascorbic acid derivative but not more than 0.01 g/L of a long acting ascorbic acid derivative. In another example, the cell culture media may contain a short acting ascorbic acid derivative but not more than 0.005 g/L of a long acting ascorbic acid derivative. In another example, the cell culture media may contain a short acting ascorbic acid derivative but not a long acting ascorbic acid derivative.

In another example, the cell culture media contains L-ascorbate sodium salt but does not contain a substantial amount of L-ascorbic acid-2-phosphate.

The cell culture media used in methods of producing stem cells expressing elevated levels of Ang1 can be a serum-containing culture media or a serum-free culture media.

The culture media may contain or may not contain a serum replacement. The serum replacement can be, for example, albumin (for example, lipid-rich albumin), transferrin, fatty acid, insulin, collagen precursor, trace element, 2-mercaptoethanol or 3-thiol glycerol, or those appropriately containing serum equivalents. Such a serum replacement can be prepared, for example, by a method described in International Publication WO 93/30679, and commercially available products can also be used.

In an example, the cell culture media used in methods of producing stem cells expressing elevated levels of Ang1 is supplemented with at least about 9% v/v, at least about 8% v/v, at least about 7% v/v, at least about 6% v/v, at least about 5% v/v, at least about 4% v/v, at least about 3% v/v, at least about 2% v/v, at least about 1% v/v FCS. It also is envisaged that the term fetal calf serum (FCS) and fetal bovine serum (FBS) can in the context of the present disclosure be used interchangeably.

In an embodiment, the cell culture media is supplemented with a non-fetal serum. It is envisaged that the culture media may be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v non-fetal serum.

For example, the culture media can be supplemented with mammalian non-fetal serum.

For example, the culture media can be supplemented with human non-fetal serum.

For example, the culture media can be supplemented with neo-natal serum. It is envisaged that the culture media may be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v neo-natal serum.

In an embodiment, the cell culture media is supplemented with mammalian neo-natal serum.

For example, the culture media can be supplemented with new born calf serum (NBCS). It is envisaged that the culture media may be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v NBCS.

In an embodiment, the cell culture media is supplemented with human neo-natal serum.

For example, the cell culture media can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v human neo-natal serum. For example, human neo-natal serum obtained from umbilical cord blood "cord blood".

In an embodiment, the culture media is supplemented with adult serum. It is envisaged that the culture media may be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v adult serum.

In an embodiment, the cell culture media is supplemented with mammalian adult serum.

For example, the cell culture media can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v mammalian adult serum.

For example, the cell culture media can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v adult bovine serum.

In an embodiment, the cell culture media is supplemented with human adult serum.

For example, the cell culture media can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v human adult serum.

For example, the cell culture media can be supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v human AB serum.

In an example, the cell culture media is supplemented with at least about 3% human AB serum.

In an embodiment the culture media is supplemented with a mixture of FCS and NBCS.

For example, the culture media can be supplemented with a mixture of FCS and NBCS so that the FCS:NBCS ratio is at least about 0.4:1, at least about 0.5:1, at least about 0.6:1, at least about 0.7:1, at least about 0.8:1, at least about 0.9:1, at least about 1:1, at least about 1.5:1, at least about 2:1.

For example, it is envisaged that the mixture of FCS and NBCS can comprise at least about 1% v/v, at least about 2% v/v, at least about 3% v/v, at least about 4% v/v, at least about 5% v/v, at least about 6% v/v, at least about 7% v/v, at least about 8% v/v, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25% v/v of the cell culture media. However, in this example, the cell culture media is supplemented with at least about 1% v/v, at least about 2% v/v, at least about 3% v/v, at least about 4% v/v, at least about 5% v/v, at least about 6% v/v, at least about 7% v/v, at least about 8% v/v, at least about 9% v/v, but less than 10% v/v FCS.

In an embodiment, the cell culture media is FCS serum free.

In an embodiment, the cell culture media is fetal serum free.

In an embodiment, the cell culture media is supplemented with non-fetal serum.

In one embodiment the cell culture media is fetal serum free and supplemented with non-fetal serum.

It another embodiment the cell culture media is supplemented with one or more stimulatory factors selected from the group consisting of 1α,25-dihydroxyvitamin D3 (1,25D), platelet derived growth factor (PDGF), tumor necrosis factor α (TNF-α), interleukin-1β (IL-1β) and stromal derived factor 1α (SDF-1α). In another embodiment, cells may also be cultured in the presence of at least one cytokine in an amount sufficient to support growth of the cells.

In another embodiment, cells are cultured in the presence of platelet cell lysate in an amount sufficient to support growth of the cells. For example, cells can be cultured in human platelet cell lysate in an amount sufficient to support growth of the cells.

In an example, cells are cultured with human AB serum and human platelet cell lysate in an amount sufficient to support growth of the cells.

One of skill in the art can also produce stem cells expressing elevated levels of Ang1 using the methods exemplified below.

Assaying Therapeutic/Prophylactic Potential of Cells

Methods for determining the ability of stem cells expressing elevated levels of Ang1 to treat or prevent or delay the onset or progression of disorders will be apparent to one of skill in the art. For example, stem cells can be assessed for their ability to increase Ang1 levels.

In one example, genetically unmodified stem cells expressing Ang1 in an amount of at least 0.1 µg/$10^6$ cells are tested for their ability to increase Ang1 expression in-vitro and/or in-vivo. In these examples, the cells or tissue are assessed for development of expression of Ang1 after the administration of stem cells expressing elevated levels of Ang1.

It will be apparent to the skilled artisan from the foregoing that the present disclosure also provides a method for identifying or isolating a cell for the treatment, prevention or delay of a disorder, the method comprising:

(i) administering stem cells expressing elevated levels of Ang1 to a test subject suffering from a disorder associated and assessing a symptom of the disorder in the subject;

(ii) comparing the symptom of a disorder of the subject at (i) to the symptom of the disorder or activity of a control subject suffering from the disorder to which the stem cells have not been administered, wherein an improvement in the symptom in the test subject compared to the control subject indicates that the stem cell treats the disorder. The cells may be any cells described herein according to any example.

EXAMPLES

Example 1: Immunoselection of MPCs by Selection of STRO-3+ Cells

Bone marrow (BM) is harvested from healthy normal adult volunteers (20-35 years old). Briefly, 40 ml of BM is aspirated from the posterior iliac crest into lithium-heparin anticoagulant-containing tubes.

Bone marrow mononuclear cells (BMMNC) are prepared by density gradient separation using Lymphoprep™ (Nycomed Pharma, Oslo, Norway) as previously described (Zannettino et al. Blood, 92: 2613-2628, 1998). Following centrifugation at 400×g for 30 minutes at 4° C., the buffy layer is removed with a transfer pipette and washed three times in "HHF", composed of Hank's balanced salt solution (HBSS; Life Technologies, Gaithersburg, MD), containing 5% fetal calf serum (FCS, CSL Limited, Victoria, Australia).

STRO-3+ (or TNAP+) cells were subsequently isolated by magnetic activated cell sorting as previously described (Gronthos et al., Journal of Cell Science 116: 1827-1835, 2003; Gronthos and Simmons, Blood, 85, 929-940, 1995). Briefly, approximately 1-3×$10^8$ BMMNC are incubated in blocking buffer, consisting of 10% (v/v) normal rabbit serum in HHF for 20 minutes on ice. The cells are incubated with 200 µl of a 10 µg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mn^{2+}$-free PBS supplemented with 1% BSA, 5 mM EDTA and 0.01% sodium azide) as above and resuspended in a final volume of 0.9 ml MACS buffer.

One hundred µl streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International Publication No. WO 2006/108229). After addition of a further 1 ml MACS buffer, the column is removed from the magnet and the TNAP+ cells are isolated by positive pressure. An aliquot of cells from each fraction can be stained with streptavidin-FITC and the purity assessed by flow cytometry.

The MPCs isolated in this manner are STRO-1$^{bright}$ MPCs.

Example 2: Starting Culture Media—Process A

The Alpha modification of Eagle's minimum essential media (MEM) with Earle's balanced salts, commonly referred to as Eagle's Alpha MEM, contains non-essential amino acids, sodium pyruvate, and additional vitamins. These modifications were first described for use in growing hybrid mouse and hamster cells (Stanners et al., Nat New Biol., 230, 52-54, 1971).

Eagle's Alpha MEM media suitable for culturing primary stem cells can be obtained from a variety of sources, including Life Technologies and Sigma.

A detailed method of establishing primary stem cell cultures, including the required growth factors used in the Exemplified processes is described in Gronthos and Simmons, Blood, 85, 929-940, 1995.

In Process A, Eagle's Alpha MEM media supplemented with 10% fetal calf serum, L-ascorbate-2-phosphate (100 μM), dexamethasone (10-7 M) and/or inorganic phosphate (3 mM) was used for culturing stem cells.

Example 3: Modified Culture Media—Process B

In Process B, the Eagle's Alpha MEM culture media used in Process A was modified (modified Alpha MEM) by:
replacing the long acting ascorbic acid derivative L-ascorbic acid-2-phosphate with a short acting ascorbic acid derivative Sodium L-ascorbate (50 mg/L);
reducing FCS from 10% v/v to 5% v/v;
supplementing with non-fetal serum (5% v/v).

TABLE 1

Summary of the differences between Processes A and B

| Process A | Process B |
|---|---|
| Media (Change applicable to Thaw Feed, Passage) | |
| Alpha MEM 10% v/v FCS | Modified media 50 mg/L Sodium L-ascorbate replaces L-ascorbic acid-2-phosphate 5% v/v FCS 5% v/v non-fetal serum |

TABLE 1-continued

Summary of the differences between Processes A and B

| Process A | Process B |
|---|---|
| Cryopreservation Formulation (50% Alpha-MEM/42.5% ProFreeze/7.5% DMSO) | |
| Alpha MEM 10% v/v FCS | Modified Alpha MEM 50 mg/L Sodium L-ascorbate replaces L-ascorbic acid-2-phosphate 5% v/v FCS 5% v/v non-fetal serum |

Example 4: Cell Culture

Mesenchymal precursor cells (MPCs) were obtained from a single donor and stored following cryopreservation.

In general terms, cell culture involved the following steps:
Cryopreserved MPCs were thawed, seeded at 10,000 cells/cm², and grown in either starting culture media (Process A; n=3) or modified culture media (Process B; n=3) to 90% confluence at 20% 02, 37° C.

To generate conditioned medium, growth medium was replaced with EBM-2 basal medium (Lonza) supplemented with FCS at a volume of 200 μl medium/cm². Cells were cultured for an additional 3 days after which medium was collected and centrifuged to remove any cells and the resulting supernatant collected and stored at −80° C.

Growth factor concentrations were measured using the Luminex platform using commercially available kits (Millipore).

Figure 2:
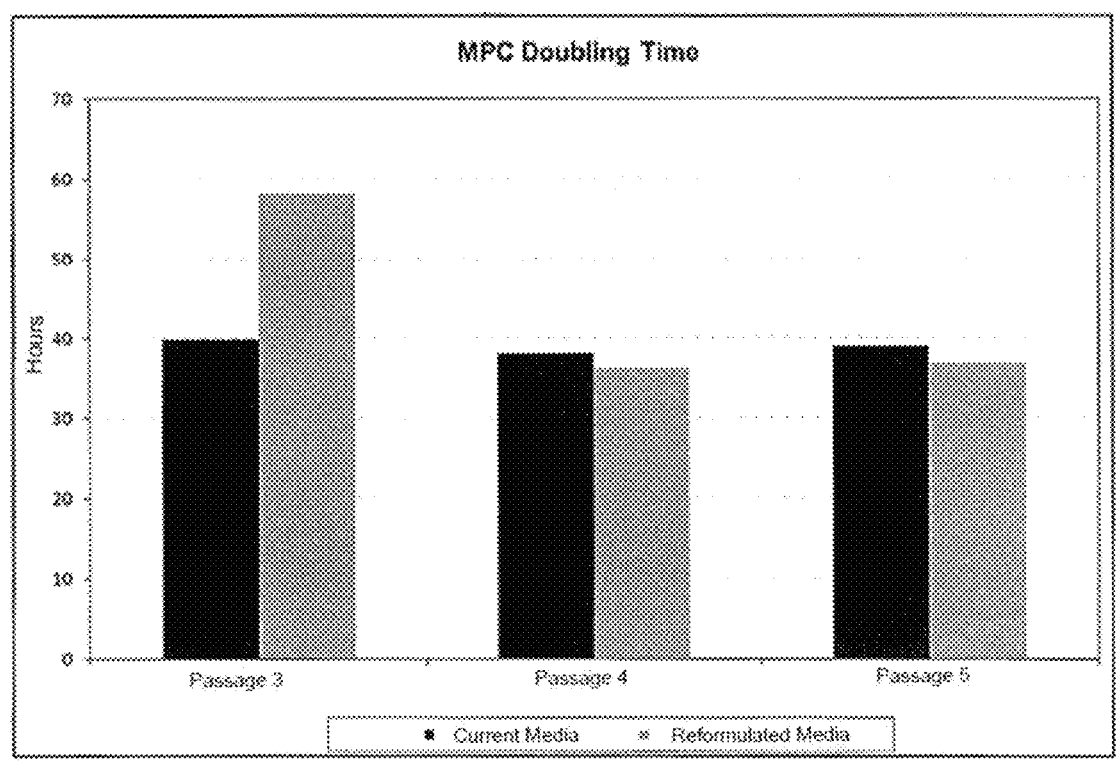
FIG. 2: MPC doubling times in current media (process A) and reformulated media (process B). MPCs were grown in the current Alpha MEM culture (process A) or reformulated in modified alpha MEM (process B). Cells were passages from P3 to P5.
Figure 3:
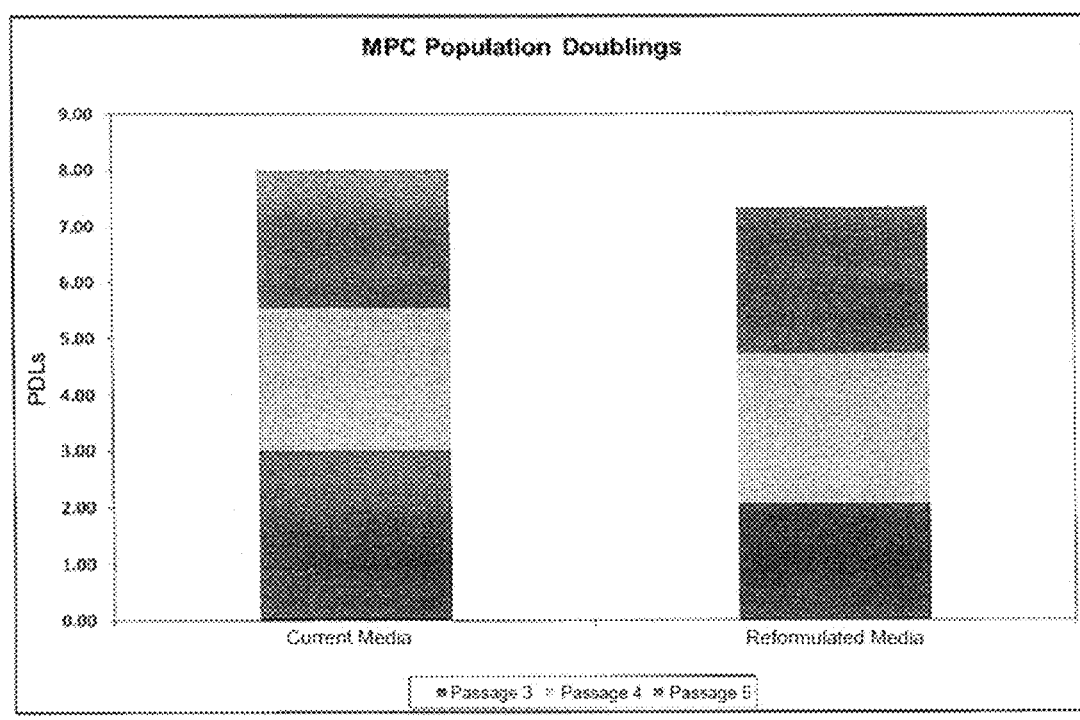
FIG. 3: Population Doubling Time (PDL) of MPCs. MPCs were grown from P3 to P5 in the current Alpha MEM culture media (process A) vs the reformulated alpha MEM (process B). MPCs grown in current (process A) media underwent 8 PDL and MPCs grown in reformulated culture media (process B) underwent 7.33 PDL.

Following cell culture, MPC growth dynamics were assessed (see FIGS. 1-3). No significant changes in cell growth, MPC doubling times or population doubling times were observed following cell culture Processes A and B.

MPCs were also characterised in terms of their expression levels of cellular markers STRO-1, CC9 and STRO-4 as well as pro-angiogenic growth factors Ang1 and VEGF.

STRO-1, CC9 and STRO-4 levels were comparable in MPCs following cell culture Processes A and B.

However, culture Process B:
increased Ang1 levels;
reduced VEGF levels;
provided a ratio of Ang1:VEGF that was consistent with Ang1:VEGF ratios previously shown to be particularly effective in enhancing vascularization.

Measurement of the levels (ug/10⁶ cells) of Ang1 and VEGF in the conditioned medium of MPCs cultured in Processes A or B are shown in Table 2.

TABLE 2

Characterisation of MPCs obtained from a single donor (three replicates) following Process A and B.

| Culture Process | Replicate | Ang 1 level ug/10⁶ cells | Average | VEGF level ug/10⁶ cells | Average | Ratio Ang1 level/VEGF level | Average |
|---|---|---|---|---|---|---|---|
| A | 1 | 0.048 | 0.045 | 0.134 | 0.14 | 0.358:1 | 0.328:1 |
| A | 2 | 0.059 | | 0.172 | | 0.343:1 | |
| A | 3 | 0.029 | | 0.102 | | 0.284:1 | |
| B | 1 | 0.733 | 0.72 | 0.027 | 0.025 | 27.1:1 | 29.6:1 |
| B | 2 | 0.717 | | 0.020 | | 35.9:1 | |
| B | 3 | 0.723 | | 0.028 | | 25.8:1 | |

Example 5: Modified Culture Conditions—Processes C and D

To control for the replacement of the long acting ascorbic acid derivative L-ascorbic acid-2-phosphate with a short acting ascorbic acid derivative Sodium L-ascorbate, MPC's from 3 different donors were serially propagated in alpha-MEM+10% FCS+50 mg/L Sodium L-ascorbate (Process C) or alpha-MEM+3% human AB serum+50 mg/L Sodium L-ascorbate (Process D)+ growth factors such as PDGF and EGF.

Ang1 and VEGF levels were assessed following cell culture in Processes C and D. The levels (ug/$10^6$ cells) of Ang1 and VEGF in the conditioned medium of MPCs cultured in Processes C or D are shown in Table 3.

Compared with Process C, culture Process D:
increased Ang1 levels;
reduced VEGF levels;
increased the ratio of Ang1:VEGF.

Compared with Process A, Processes C and D resulted in progressive increases in the expression levels of Ang1. This suggests that the presence of a short acting ascorbic acid derivative and non-fetal serum each independently result in increased Ang1 expression and together exhibit a synergistic effect in increasing Ang1 expression.

Figure 7:
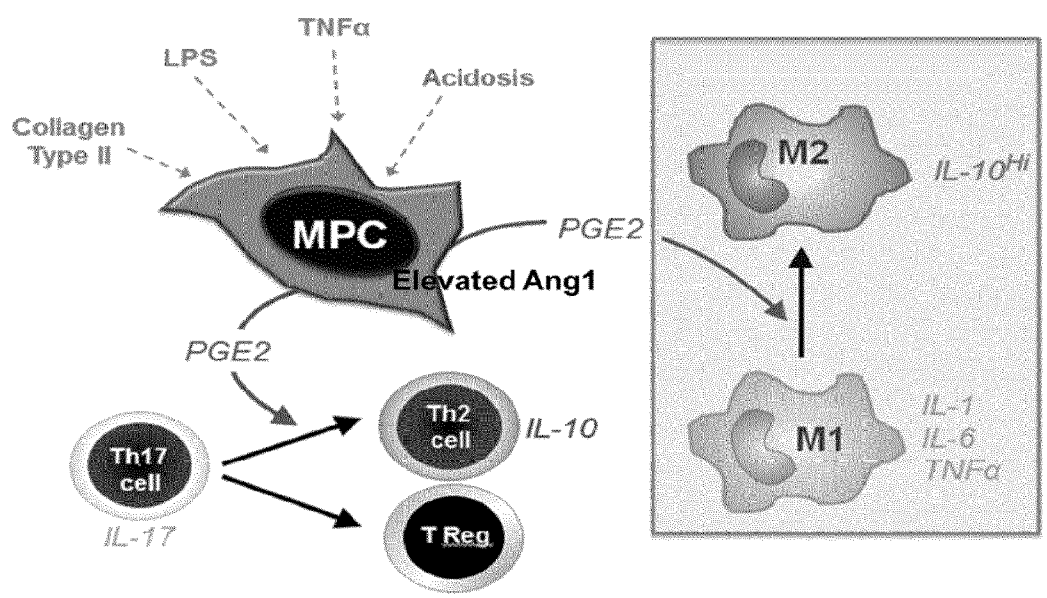
FIG. 7: MPCs role in regulating macrophage polarisation.

These data indicate that MPCs expressing elevated levels of Ang1 promote M2-type macrophage production (FIG. 7).

Stem cells expressing elevated levels of Ang1 were cultured with increasing levels of IL-1β alone or in combination with TNF-α to assess the effect of these cytokines of secretion of PGE2.

Figure 8:
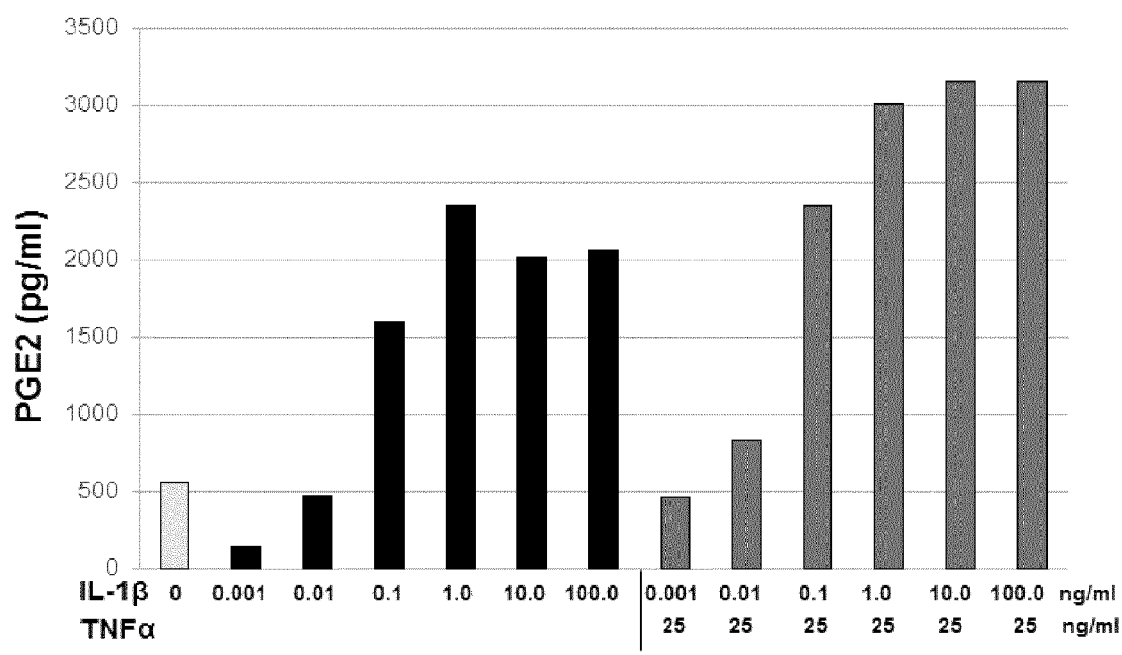
FIG. 8: Secretion of PGE2: Additive Effect of IL-1β and TNFα.

An additive effect of IL-1β and TNF-α on PGE2 expression was observed (FIG. 8).

PGE2 promotes differentiation of Th17 cells to Th2 and TReg cells as well as polarization of M1-type macrophages to M2-type macrophages (FIG. 7). Elevated IL-1 and TNF-α levels are observed in subjects with inflammatory diseases such as type II diabetes.

Accordingly, increased PGE2 secretion from stem cells expressing elevated levels of Ang1 in response to TNFα and IL1β suggests that stem cells expressing elevated levels of Ang1 may increase anti-inflammatory cell production in subjects with inflammatory diseases. In particular, stem cells expressing elevated levels of Ang1 may:

increase M2-type macrophage production by promoting polarization of M1-type macrophages to M2-type macrophages; and/or increase Th2 and Treg production by promoting differentiation of Th17 cells.

TABLE 3

Characterisation of MPCs from 3 different donors following Process C and D.

| Culture Process | Donor Sample | Ang 1 level ug/$10^6$ cells | Average | VEGF level ug/$10^6$ cells | Average | Ratio Ang1 level/VEGF level | Average |
|---|---|---|---|---|---|---|---|
| C | 1 | 0.143 | 0.136 | 0.430 | 0.328 | 0.333:1 | 0.409:1 |
| C | 2 | 0.164 | | 0.266 | | 0.523:1 | |
| C | 3 | 0.102 | | 0.287 | | 0.370:1 | |
| D | 1 | 0.266 | 0.191 | 0.164 | 0.109 | 1.73:1 | 2.11:1 |
| D | 2 | 0.164 | | 0.061 | | 3.20:1 | |
| D | 3 | 0.143 | | 0.102 | | 1.40:1 | |

Example 6: Polarization of Pro-Inflammatory M1 Monocytes to M2 Phenotype

Figure 4:
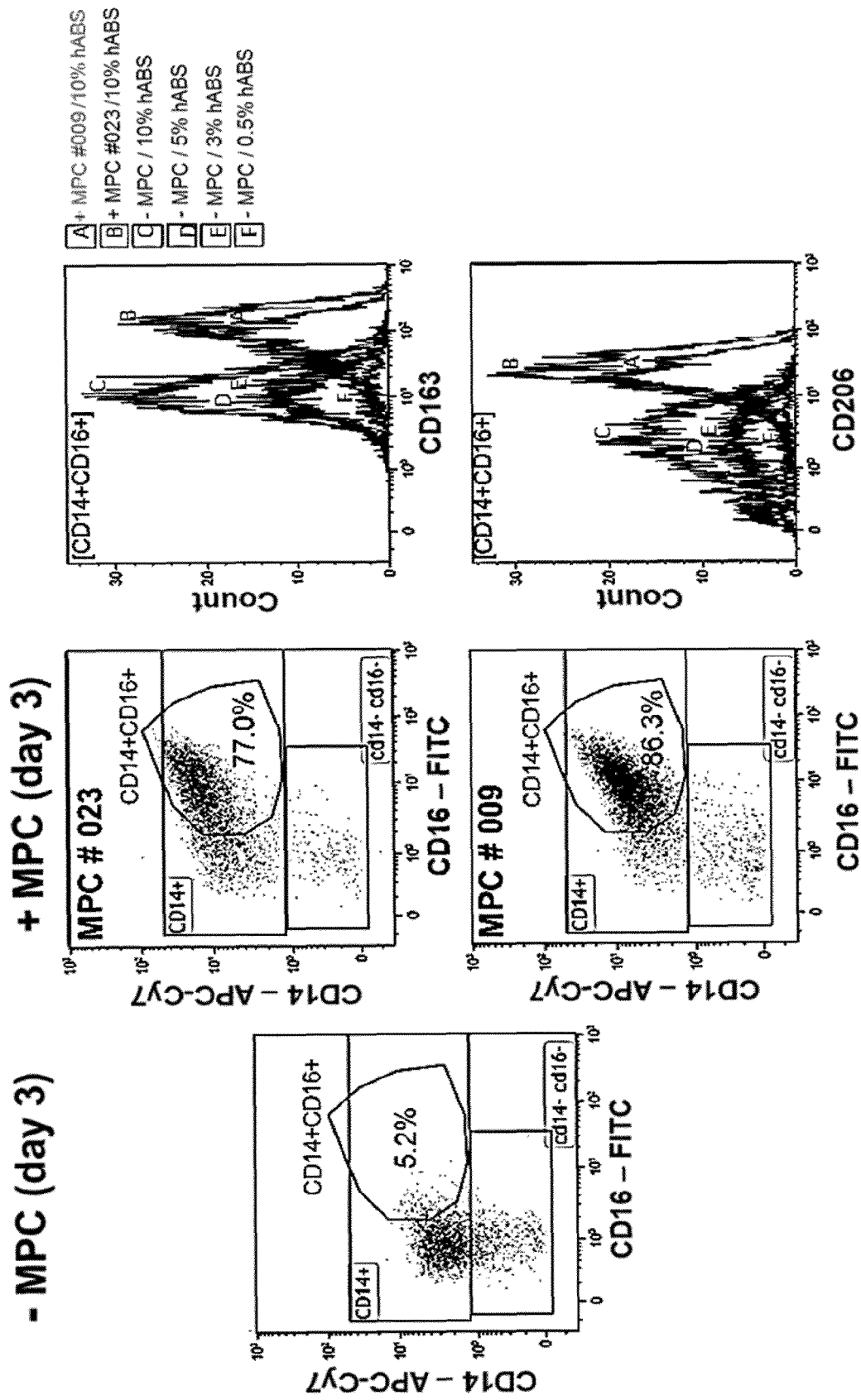
FIG. 4: Co-culture of CD14+ immunoselected monocytes with MPC results in generation of CD14+16+ macrophages which exhibit the phenotypic properties of M2 macrophages.

CD14+ monocytes were immunoselected from whole blood. Monocyte populations were characterised based on CD16 expression. 5.2% of cells exhibited phenotypic properties of M2-type macrophages (CD14+CD16+) (FIG. 4).

CD14+ monocytes were co-cultured with MPCs expressing elevated levels of Ang1 for seven days. MPCs were obtained from two separate donors (#023 and #009).

After three days of co-culture cells were assessed for:
CD14, CD16 expression; and
Secretion of TNF-α in response to lipopolysaccharide (LPS). LPS was added 1 ng/ml for 24 hours (+a transport inhibitor for the final 5 hours).

Figure 5:
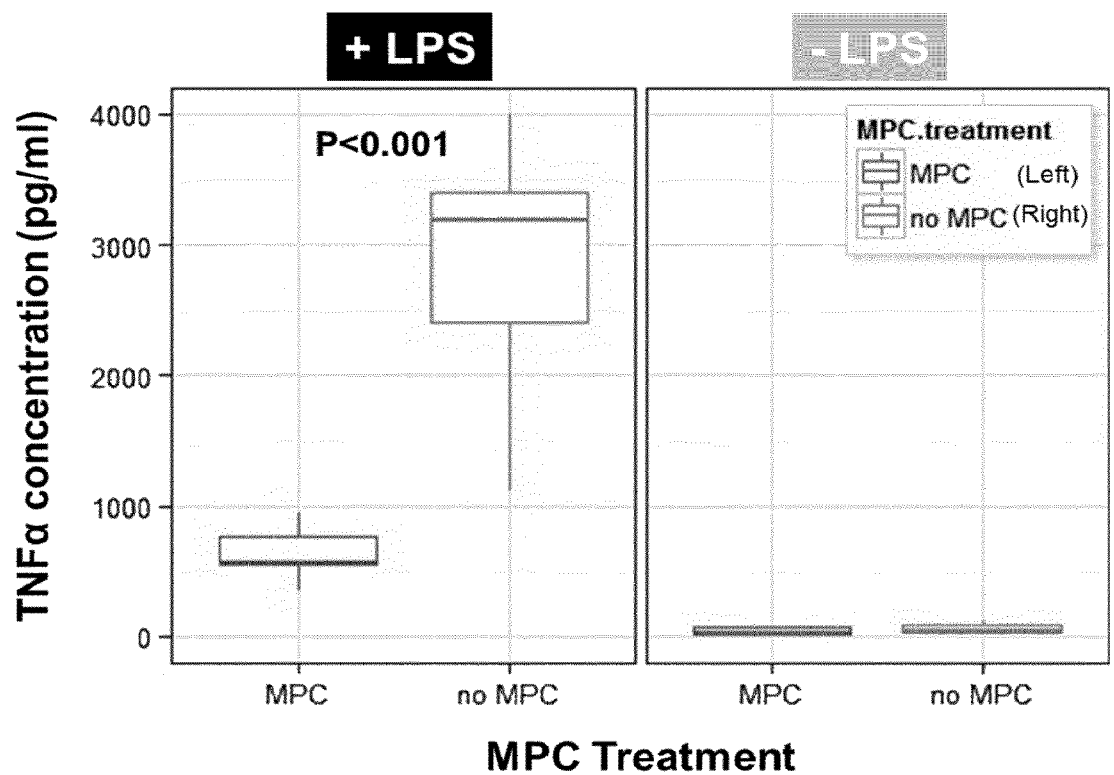
FIG. 5: Co-culture with MPC prevents inflammation-driven (LPS) secretion of TNFα by macrophages.

Co-culture resulted in:
Generation of macrophages which exhibit the phenotypic properties of M2-type macrophages (CD14+CD16+ CD163+CD206+) (FIG. 4);
Prevention of inflammation-driven (LPS) secretion of TNFα by macrophages (FIG. 5).

Figure 6:
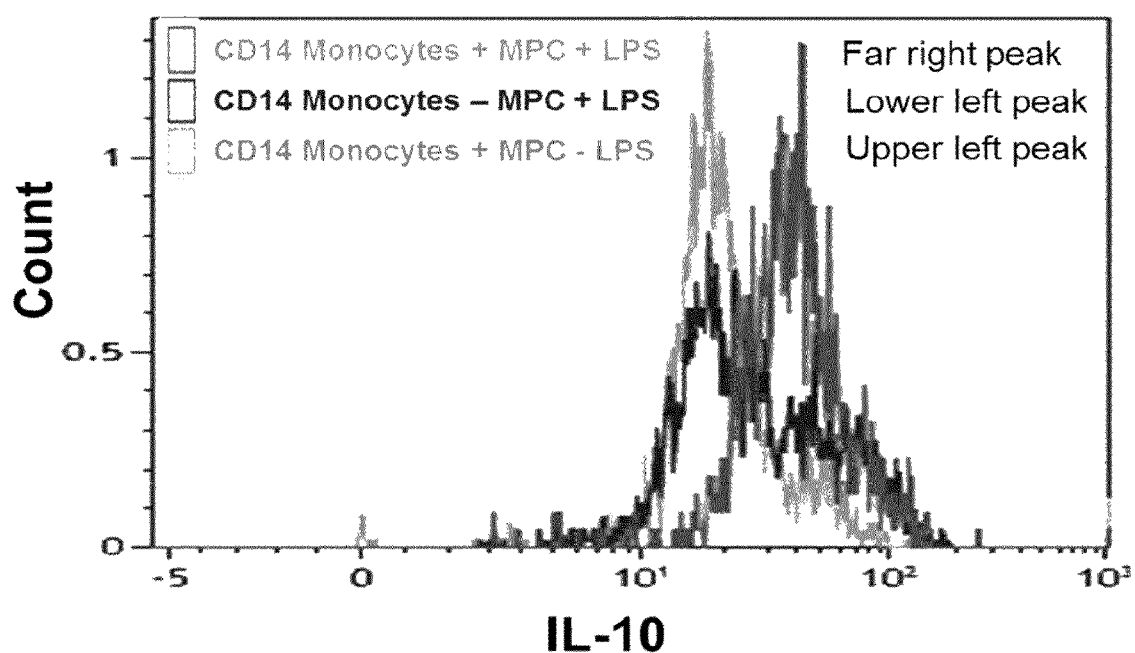
FIG. 6: Production of the anti-inflammatory cytokine IL-10 by macrophages is enhanced by co-culture with MPC in the presence of LPS.

After 7 days of co-culture cells were assessed for secretion of IL-10 in response to LPS. LPS was added 1 ng/ml for 24 hours (+a transport inhibitor for the final 5 hours). IL-10 expression was analysed by intracellular flow cytometry. IL-10 production by macrophages was enhanced by co-culture with MPC in the presence of LPS (FIG. 6).

Example 7: Sheep Model of Collagen-Induced Arthritis

Stem cells expressing elevated levels of Ang1 were administered in an ovine model of rheumatoid arthritis (Thorpe et al. Clinical & Exp. Rheumatology, 10:143-150 (1992). The model features both the systemic and joint inflammatory manifestations of Rheumatoid arthritis.

150 million cryopreserved ovine MPCs were administered intravenously via the jugular vein.

Figure 9:
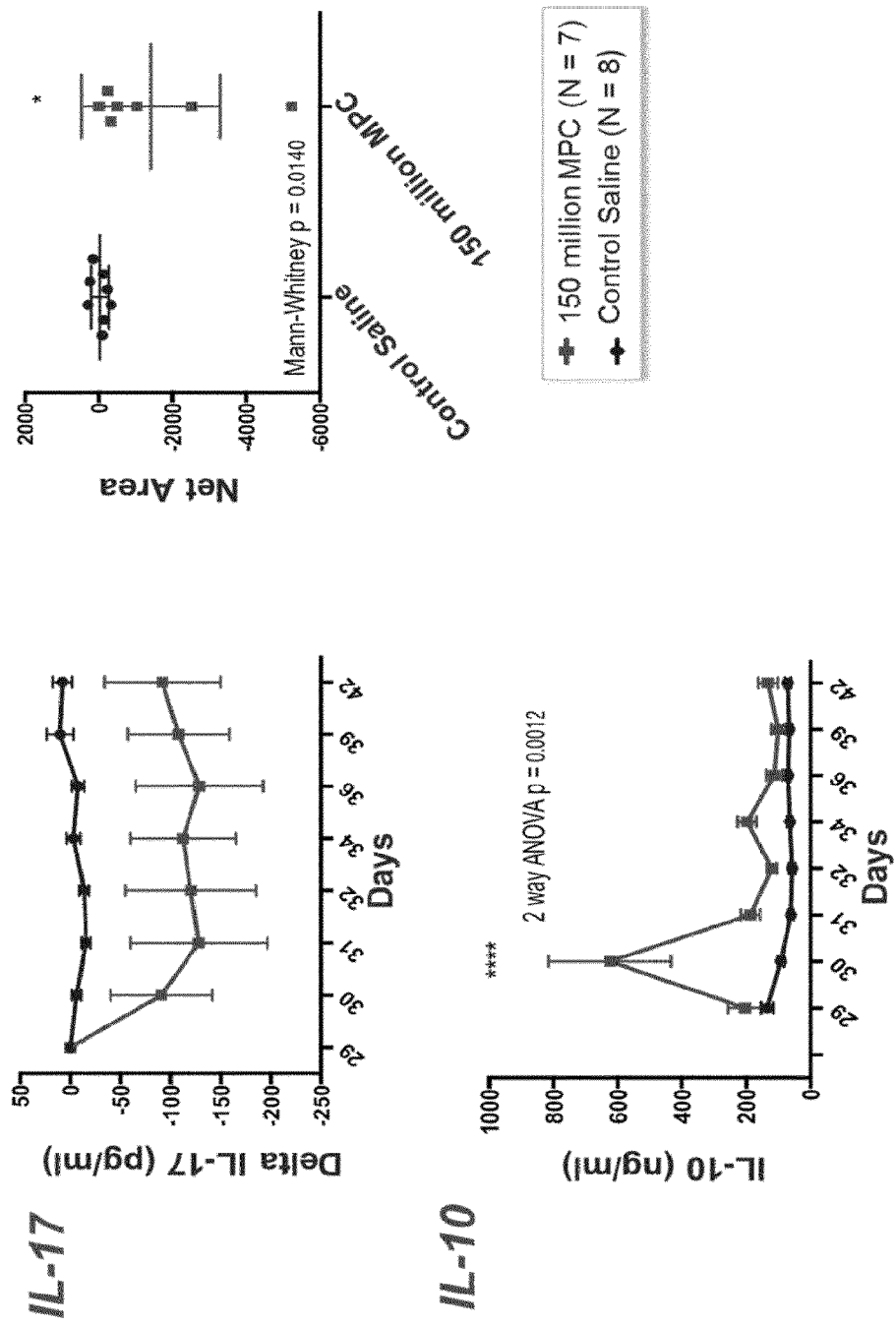
FIG. 9: Changes in the levels of pro- and anti-inflammatory cytokines following MPC administration.
Figure 10A:
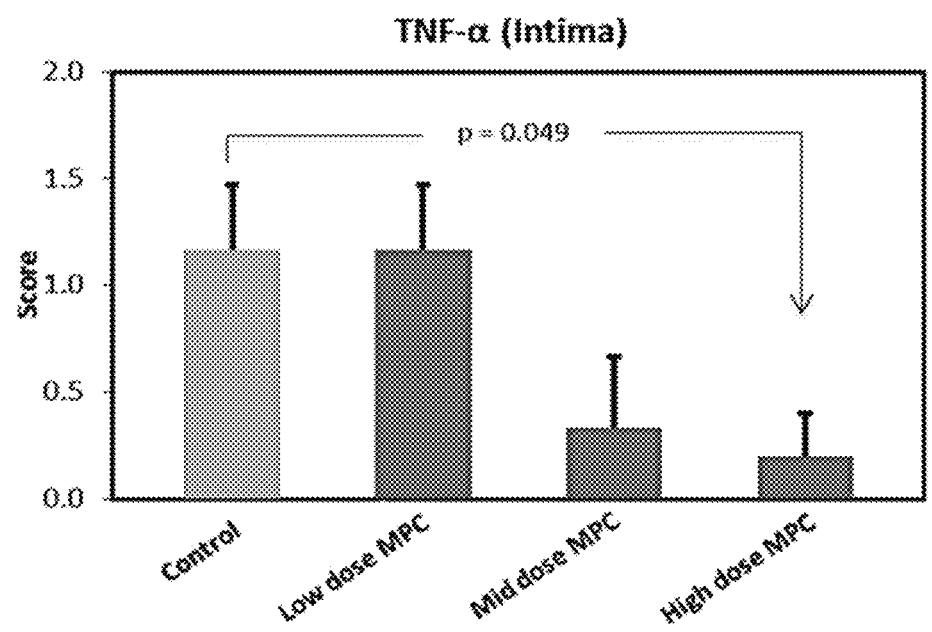
FIGS. 10A-10F: MPC Administration at the Time of Established Late Disease (d.42) Results.
in Reduced Levels of Inflammatory Cytokines in Joints.
Figure 10B:
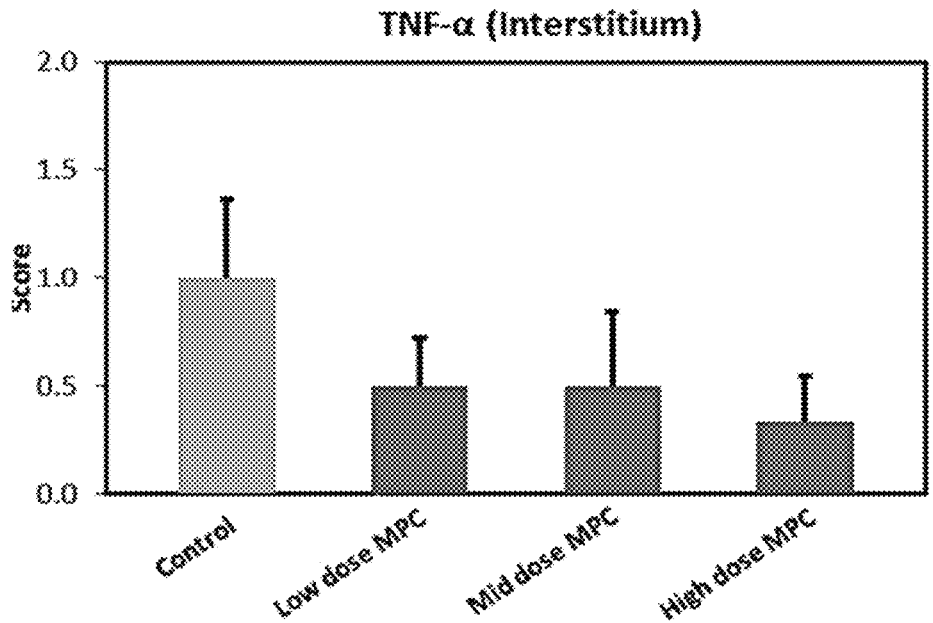
Figure 10C:
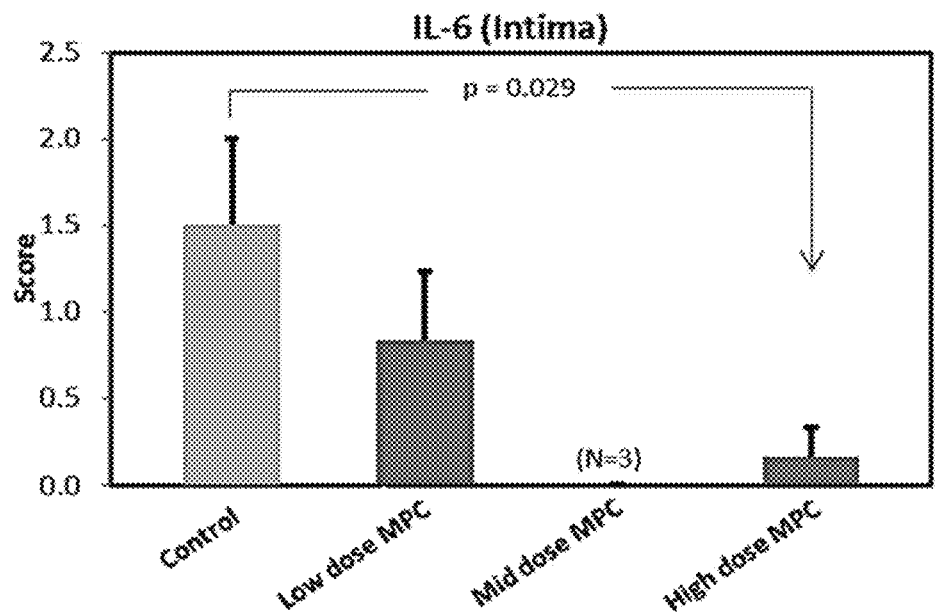
Figure 10D:
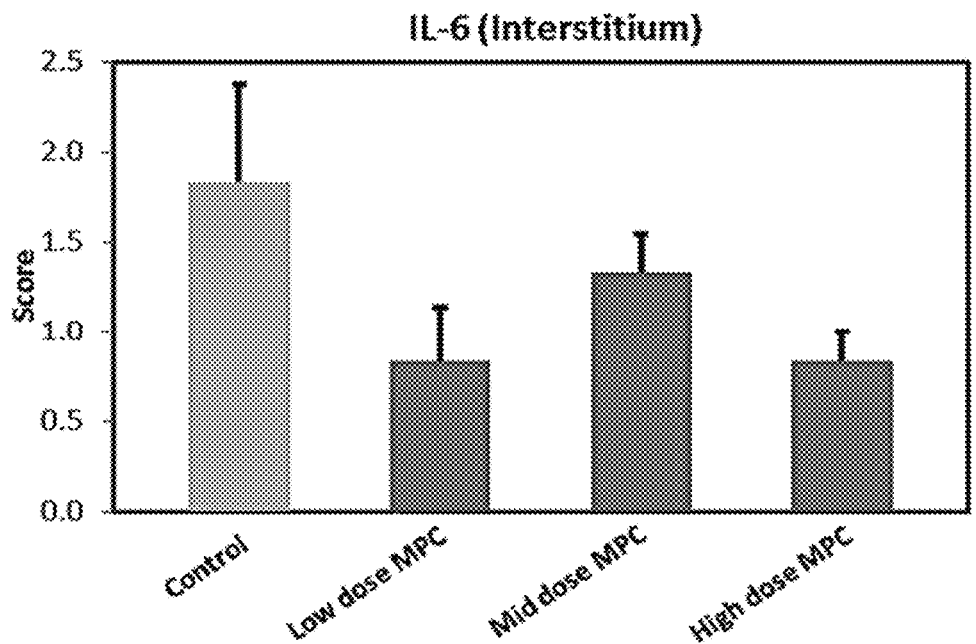
Figure 10E:
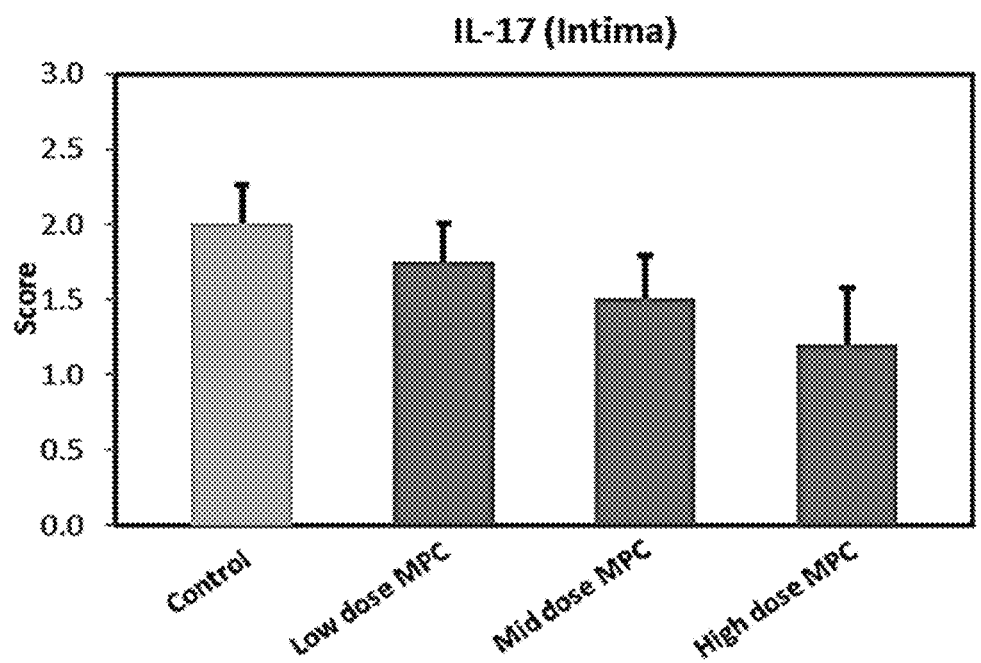
Figure 10F:
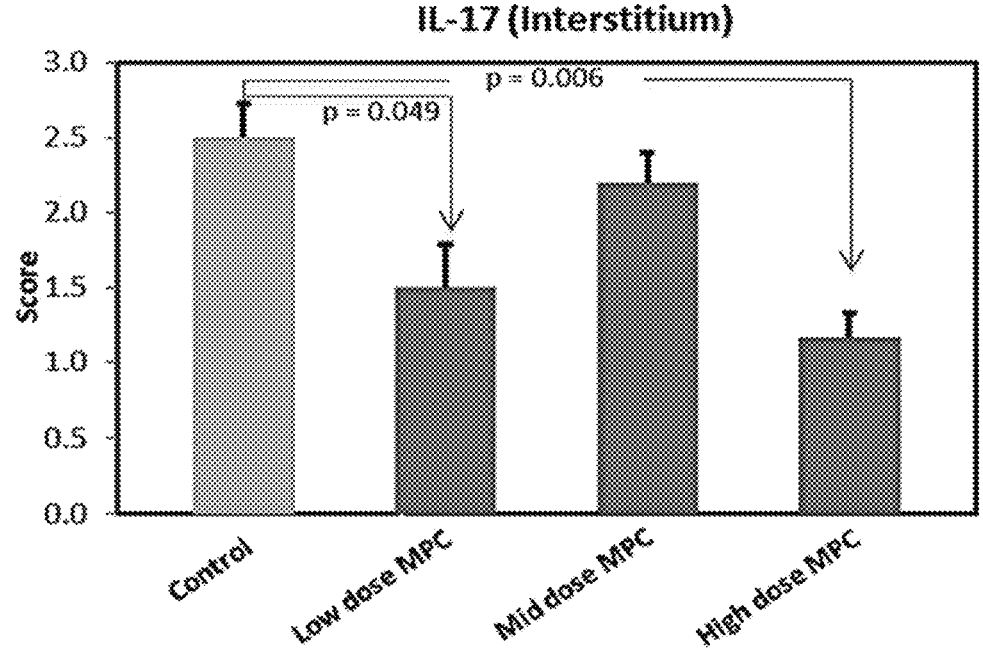

IL-17 and IL-10 levels were assessed over two weeks. Changes in the levels of pro and anti-inflammatory cytokines are shown in (FIG. 9).

Stem cells expressing elevated levels of Ang1 were also administered at the time of establishment of late disease (day 42). Administration of stem cells resulted in reduced levels of inflammatory cytokines in joints (FIG. 10).

Example 8: Stem Cell Administration in Diabetes

A single intravenous infusion of 3 doses of mesenchymal precursor cells (MPC) was compared with placebo control injected human subjects with type 2 diabetes inadequately controlled by metformin or metformin plus one other oral agent. Changes in baseline HbA1c, IL-6, TNF-alpha, fasting insulin, adiponectin, osteocalcin and hsCRP were assessed over 12 weeks.

Figure 11:
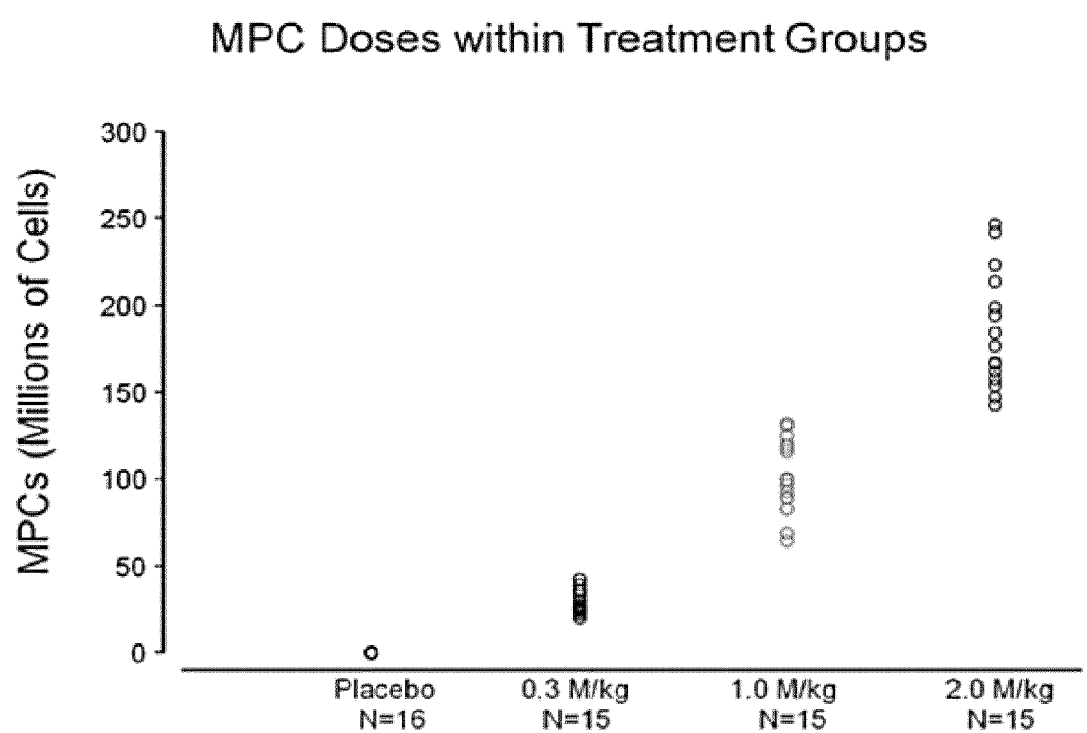
FIG. 11: Dosing of MPCs for cohort 1-3.

Subjects were separated into 3 cohorts (FIG. 11):
Cohort 1: MPC dose 1 (0.3 million cells/kg) [n=15] or placebo [n=5]
Cohort 2: MPC dose 1 (1.0 million cells/kg) [n=15] or placebo [n=5]
Cohort 3: MPC dose 1 (2.0 million cells/kg) [n=15] or placebo [n=5]

Figure 15A:
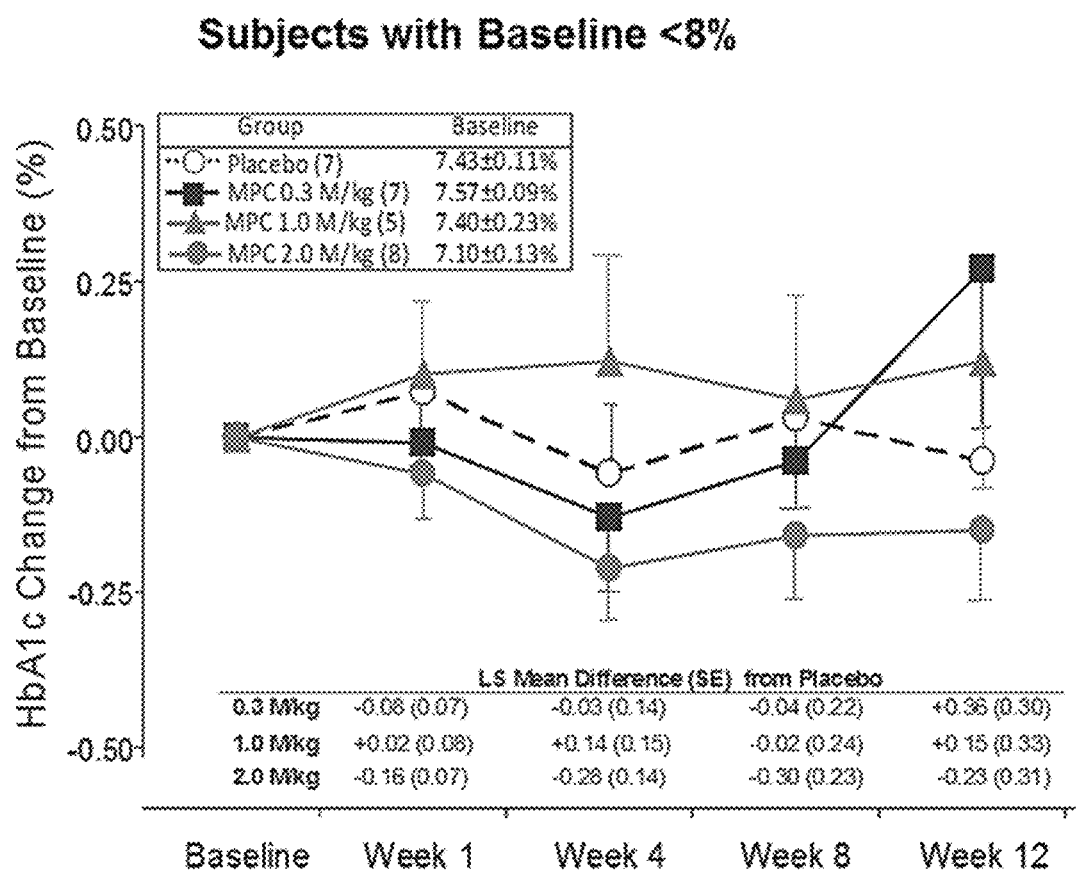
FIGS. 15A-15B: HbA1c change by subgroup of baseline HbA1c<8% (FIG. 15A) or ≥8% (FIG. 15B)
Figure 15B:
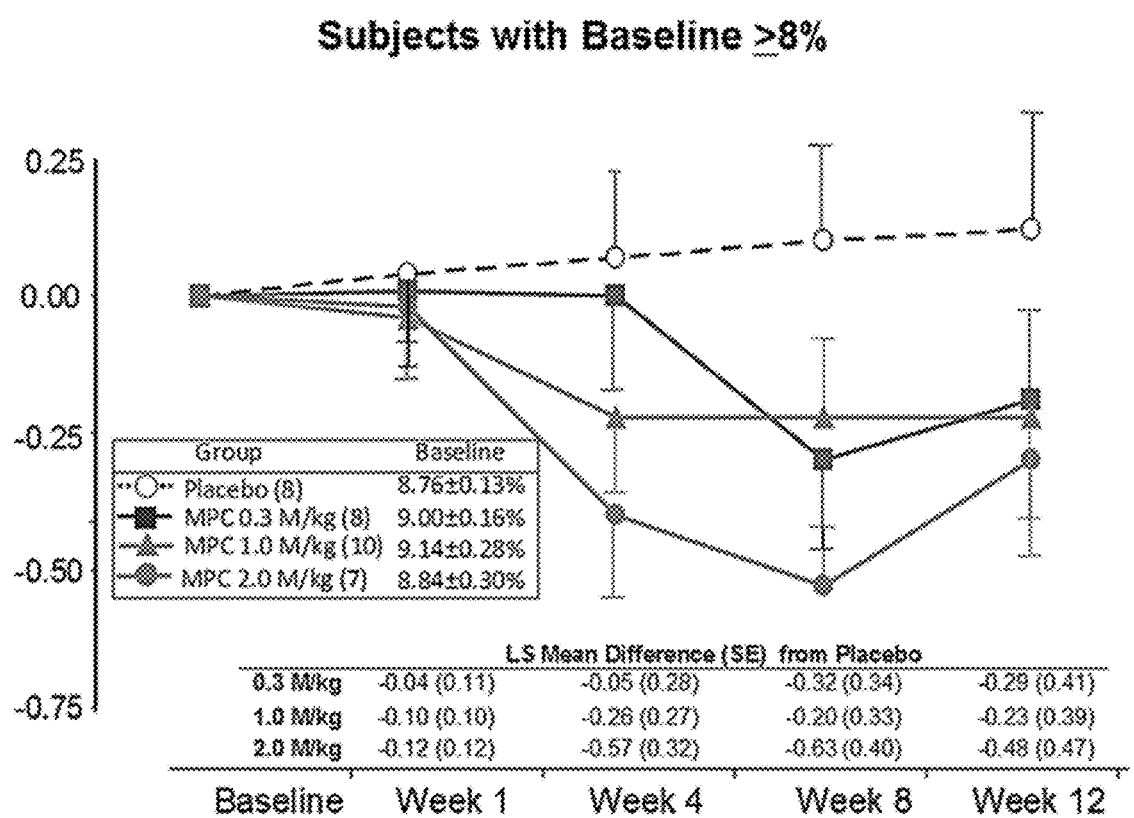
Figure 16:
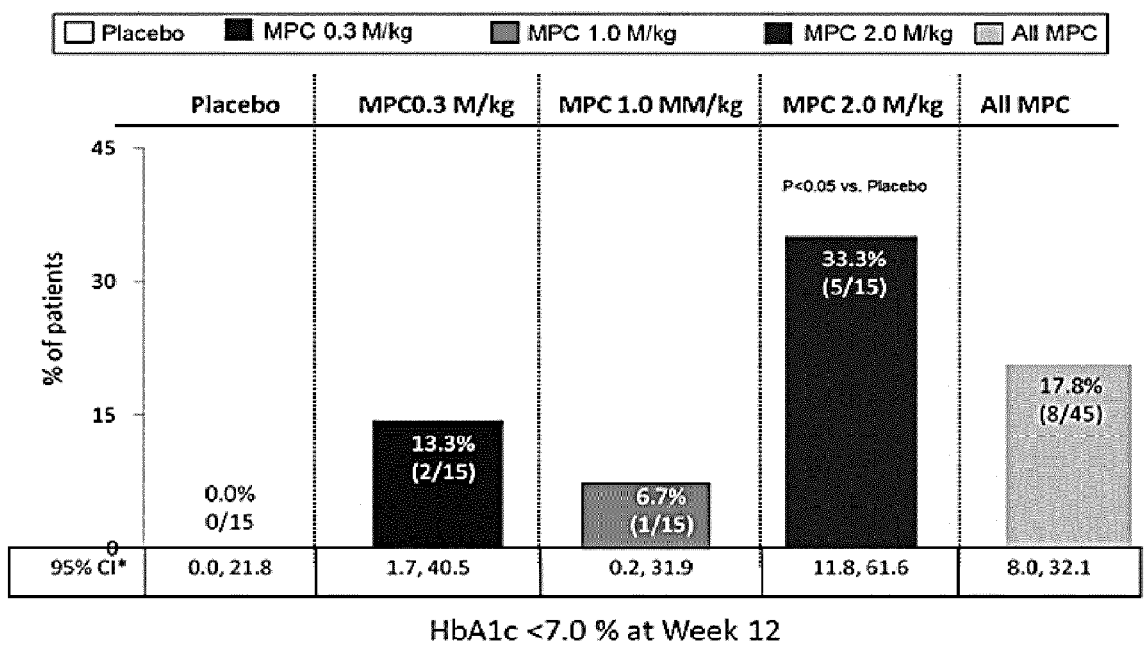
FIG. 16: Subjects at target HbA1c (<7.0%) at Week 12

A slight reduction in HbA1c was observed in MPC treated subjects compared with a slight increase in placebo control subjects (Table 4). Greater HbA1c reduction was observed in cohort 2 vs. Placebo at Week 8 (Table 4). A trend for greater HbA1c reductions was observed in subjects with baseline HbA1c values ≥8% (FIG. 15). Eight of 45 (17.8%) subjects achieved target HbA1c (<7.0%) at week 12 (FIG. 16).

Figure 12:
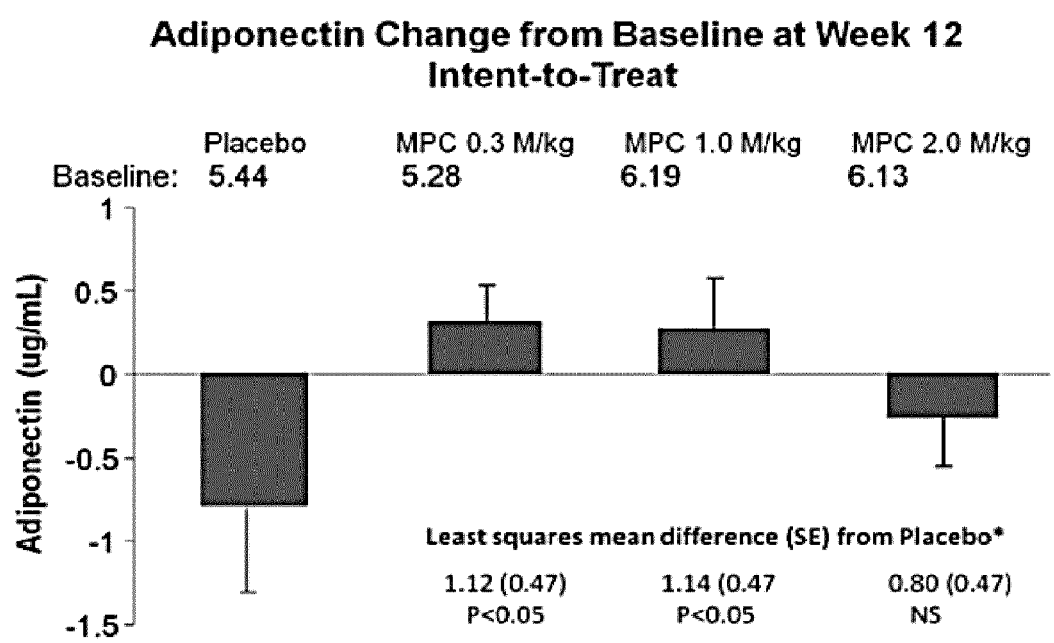
FIG. 12: Adiponectin levels at week 12 (change from baseline).
Figure 13:
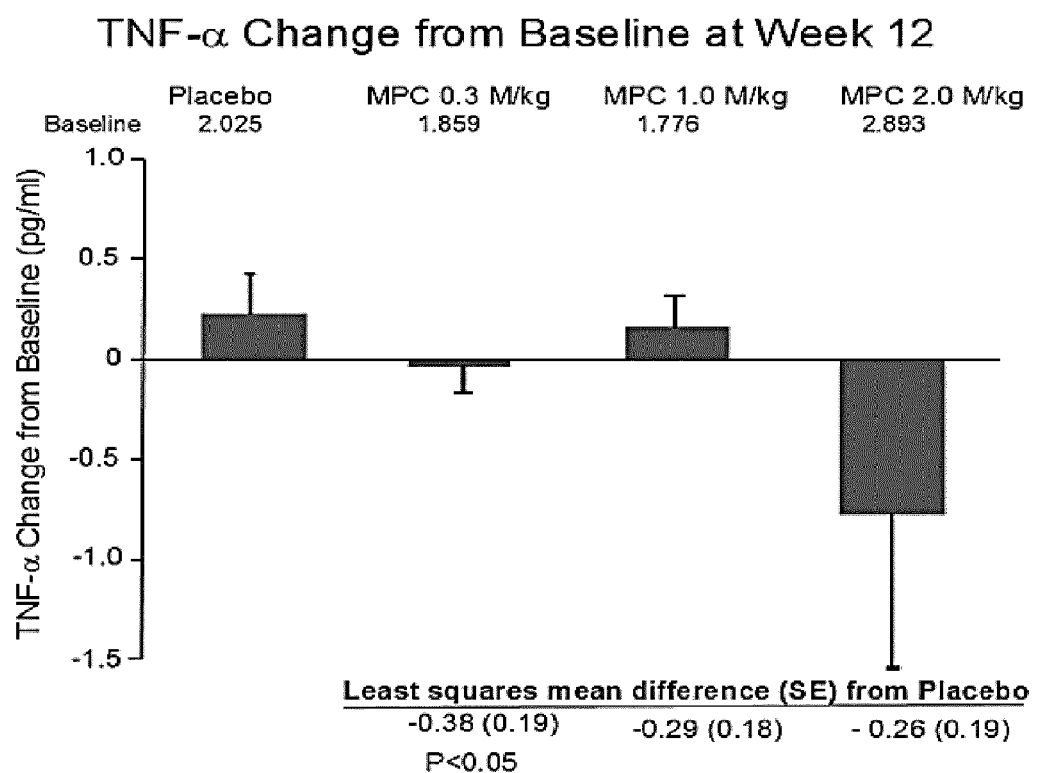
FIG. 13: TNF-alpha levels at week 12 (change from baseline).
Figure 14:
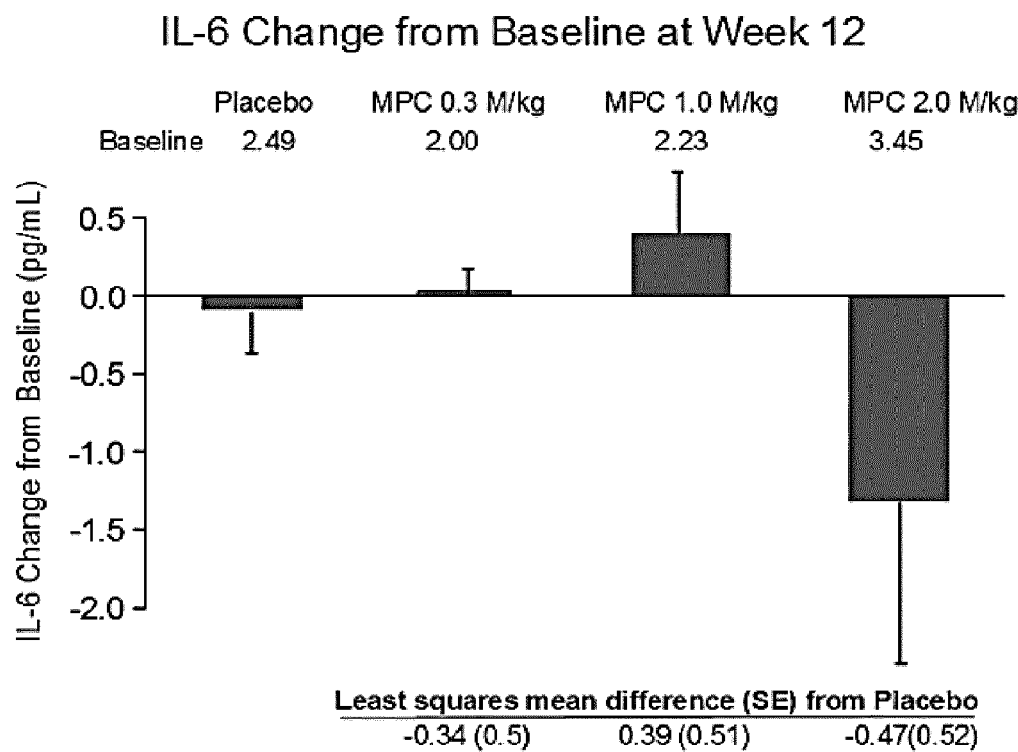
FIG. 14: IL-6 levels at week 12 (change from baseline).

Trends for improvements in fasting insulin and adiponectin levels (FIG. 12) were observed in MPC treated subjects compared with placebo control subjects. There was a reduction in TNF-alpha and IL-6 levels in MPC treated subjects compared with placebo control subjects, the most significant decrease being observed in cohort 3 (FIG. 13). In cohort 3, the change in TNF-alpha (FIG. 13) and IL-6 (FIG. 14) from baseline was −0.26 μg/ml and −0.47 μg/ml respectively (FIG. 13).

Figure 23:
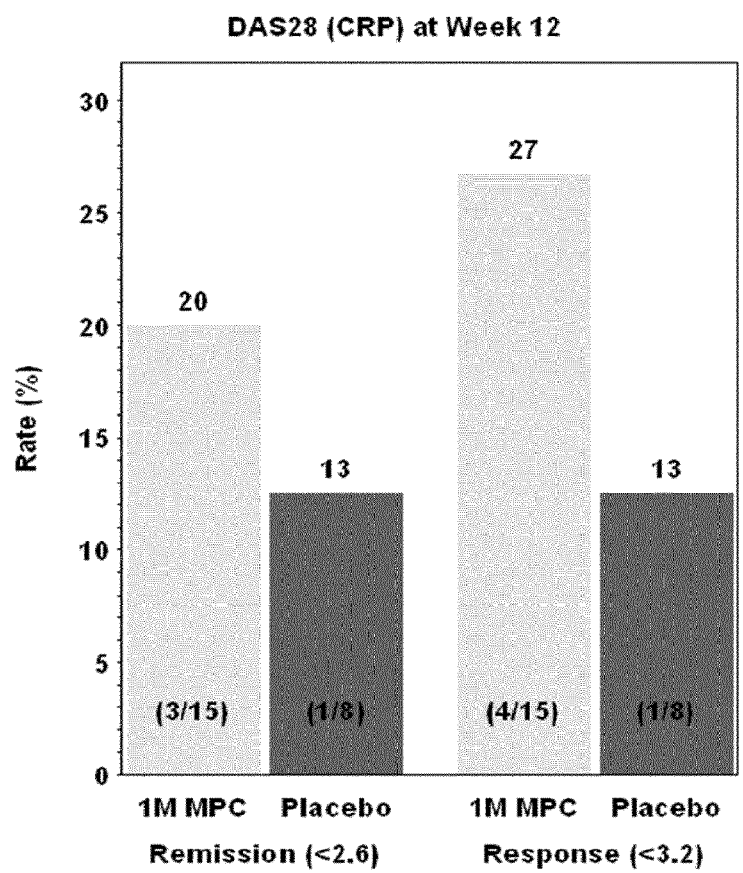
FIG. 23: DASCRP responder analysis at week 12
Figure 24:
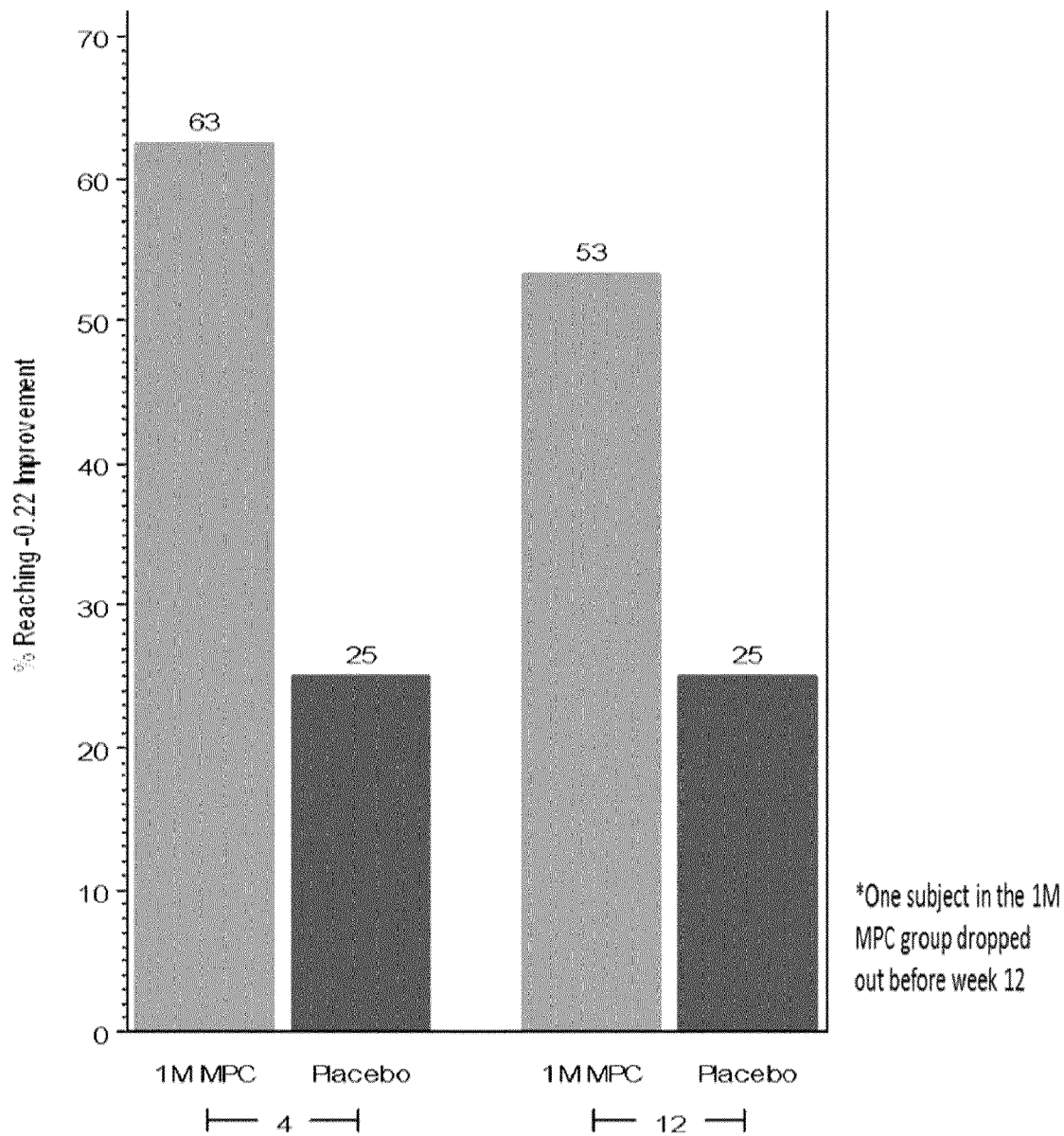
FIG. 24: Health assessment questionnaire disease index (HAQ-DI): proportion reaching MCID (−0.22)

Change from baseline in Disease Activity Score (DAS28); ESR/CRP; HAQ-DI (FIG. 24); SF-36 (Remission DAS28 (CRP)<2.6); Response DAS28 (CRP)<3.2; FIG. 23);
Hand/wrist x-rays at 6 and 12 months.

There were no treatment related serious adverse events (SAEs) associated with cohort 1. Early and sustained efficacy was seen over 3 months.

Figure 17A:
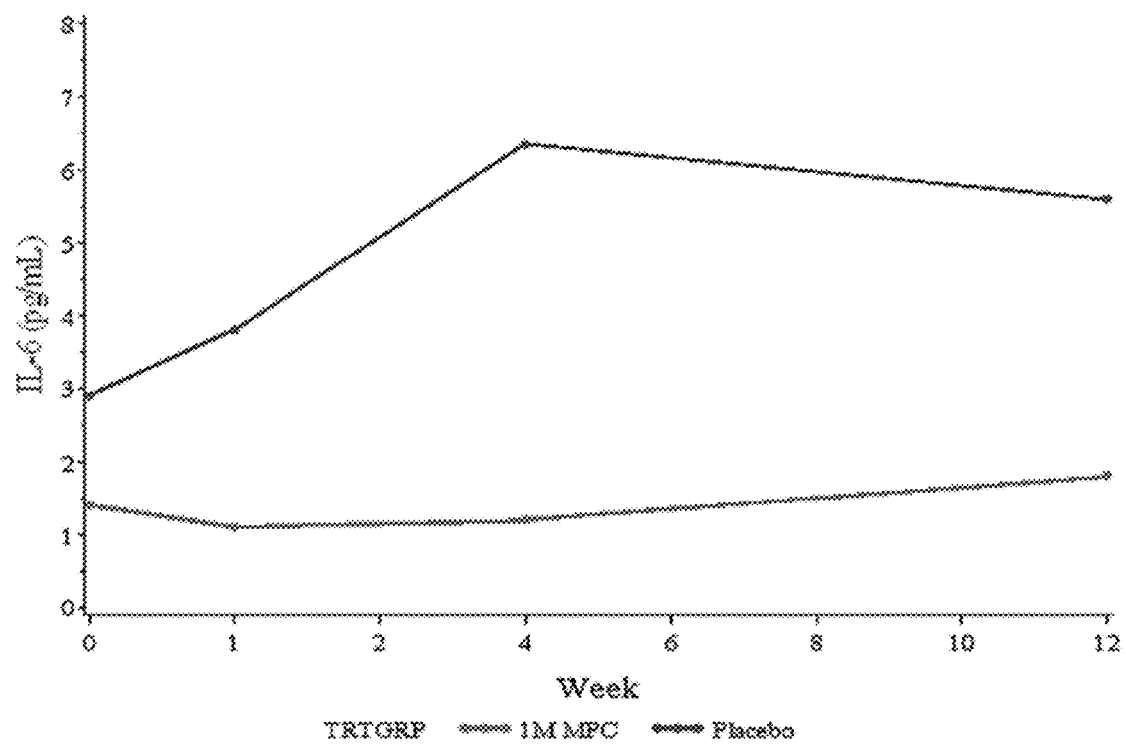
FIGS. 17A-17B: Median IL-6 change over time
Figure 17B:
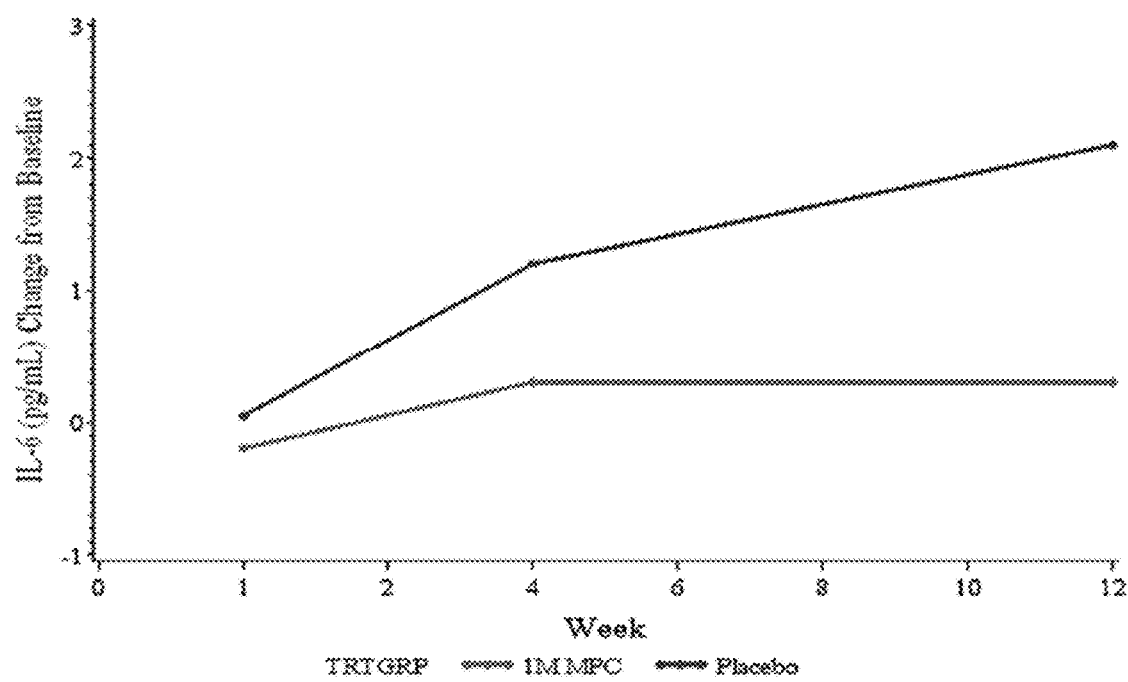

IL-6 levels were reduced from baseline in cohort 1 compared with placebo across weeks 1-12 (FIG. 17).

Data supports suggestion of potential remission rate of about 20% which may be higher than other biologics (FIG. 23).

The twelve week primary endpoint for cohort 1 reveals a consistent trend of improved response over placebo.

The follow up interim analysis demonstrates durability of effect in responders over time.

Cohort 2 is underway testing a higher single dose.

Example 10: Stem Cell Administration in Diabetic Nephropathy

A single intravenous infusion of 2 doses of mesenchymal precursor cells (MPC) was compared with placebo control

TABLE 4

Summary of Baseline HbA1c (%) and Change from Baseline by Visit.
Values are Least Squares Mean Difference (SE) from Placebo

|  | Placebo | MPC 0.3 M/kg | MPC 1.0 M/kg | MPC 2.0 M/kg |
| --- | --- | --- | --- | --- |
| Baseline Mean (SD) | 8.14 (0.766) | 8.33 (8.23) | 8.56 (1.141) | 7.91 (1.068) |
| LS Mean (SE) Diff. from Placebo [1] |  |  |  |  |
| Week 1 |  | −0.06 (0.063) | −0.06 (0.065) | −0.12 (0.04) |
|  |  | p = 0.331 | p = 0.379 | p = 0.063 |
| Week 4 |  | −0.06 (0.165) | −0.08 (0.167) | −0.33 (0.171) |
|  |  | p = 0.797 | p = 0.6307 | p = 0.0558 |
| Week 8 |  | −0.07 (0.205) | −0.10 (0.208) | −0.43 (0.212) |
|  |  | p = 0.329 | p = 0.627 | p = 0.049 |
| Week 12 Endpoint [2] |  | 0.03 (0.251) | −0.06 (0.254) | −0.29 (0.255) |
|  |  | p = 0.915 | p = 0.817 | p = 0.258 |

[1] LS Mean Difference, SE, and 95% CI are obtained from an ANCOVA model with treatment and screening HbA1c category (<8% or >=8%) as factors, and baseline value as covariate
[2] Week 12 Endpoint defined as measurement at Week 12 or the last post-baseline assessment prior to administration of rescue medication during the 12 week study period
Source: Tables 15.2.11; 15.2.1.1.x Example 9: Stem Cell Administration in Rheumatoid Arthritis A single intravenous infusion of 2 doses of mesenchymal precursor cells (MPC) was compared with placebo control injected human subjects with rheumatoid arthritis classified as incomplete anti-TNFα responders or those subjects who had failed up to 2 additional biologics.

48 subjects included in the trial were: +RF/anti-CCP; >4 swollen/tender joints; ESR/CRP>ULN.

Figure 18:
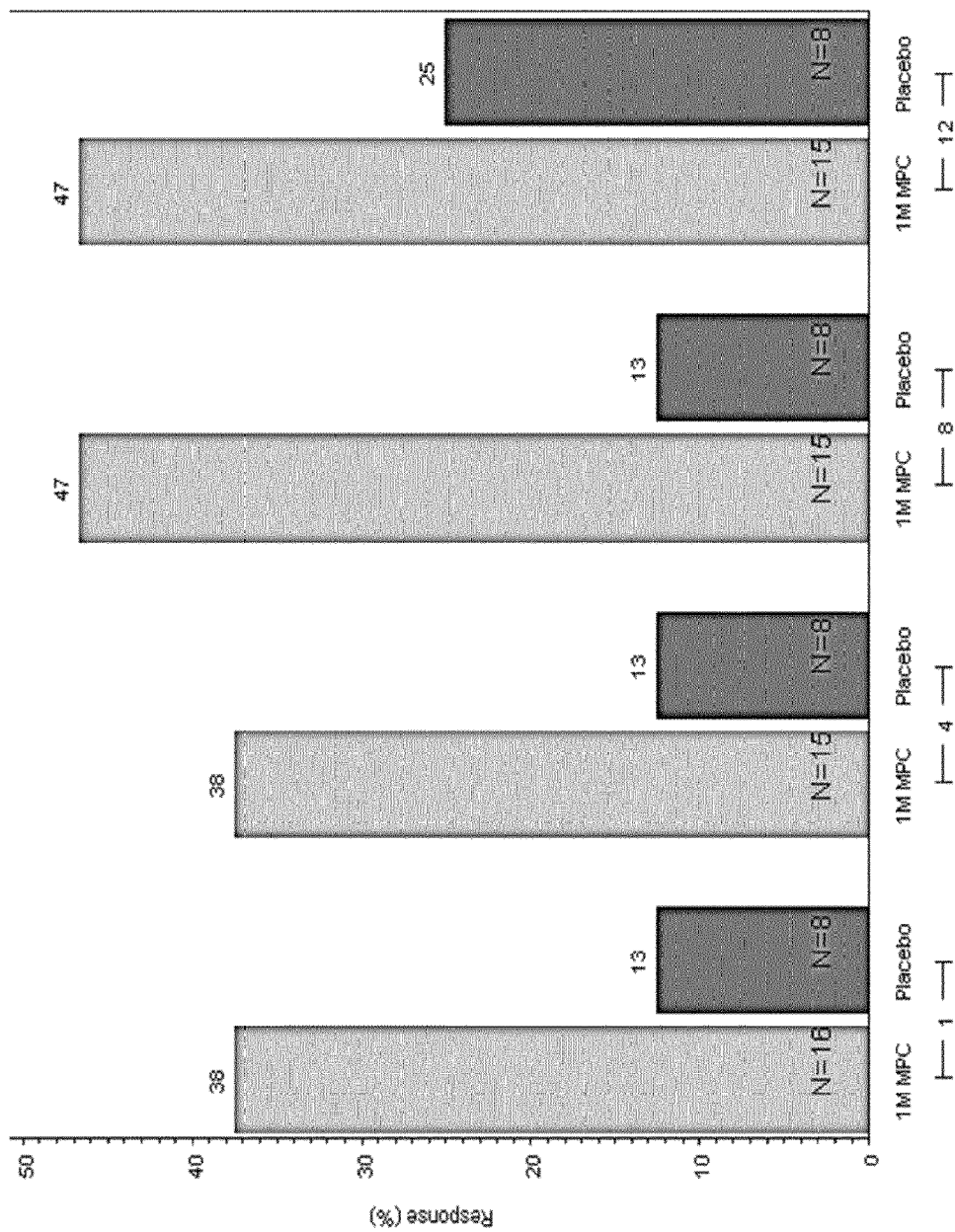
FIG. 18: ACR 20 response biologic refractory RA: 1M MPCs/kg
Figure 19:
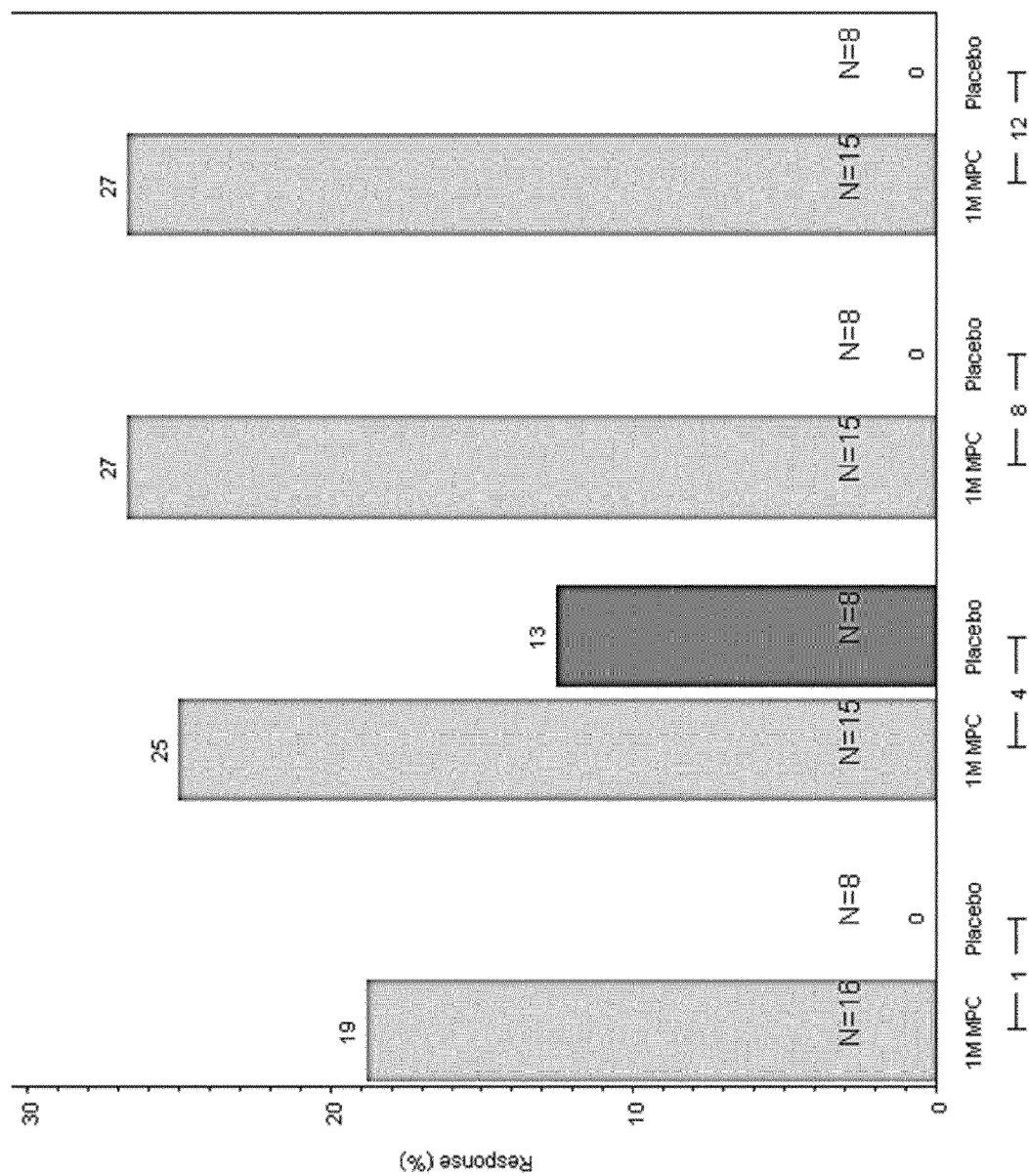
FIG. 19: ACR 50 response biologic refractory RA: 1M MPCs/kg
Figure 20:
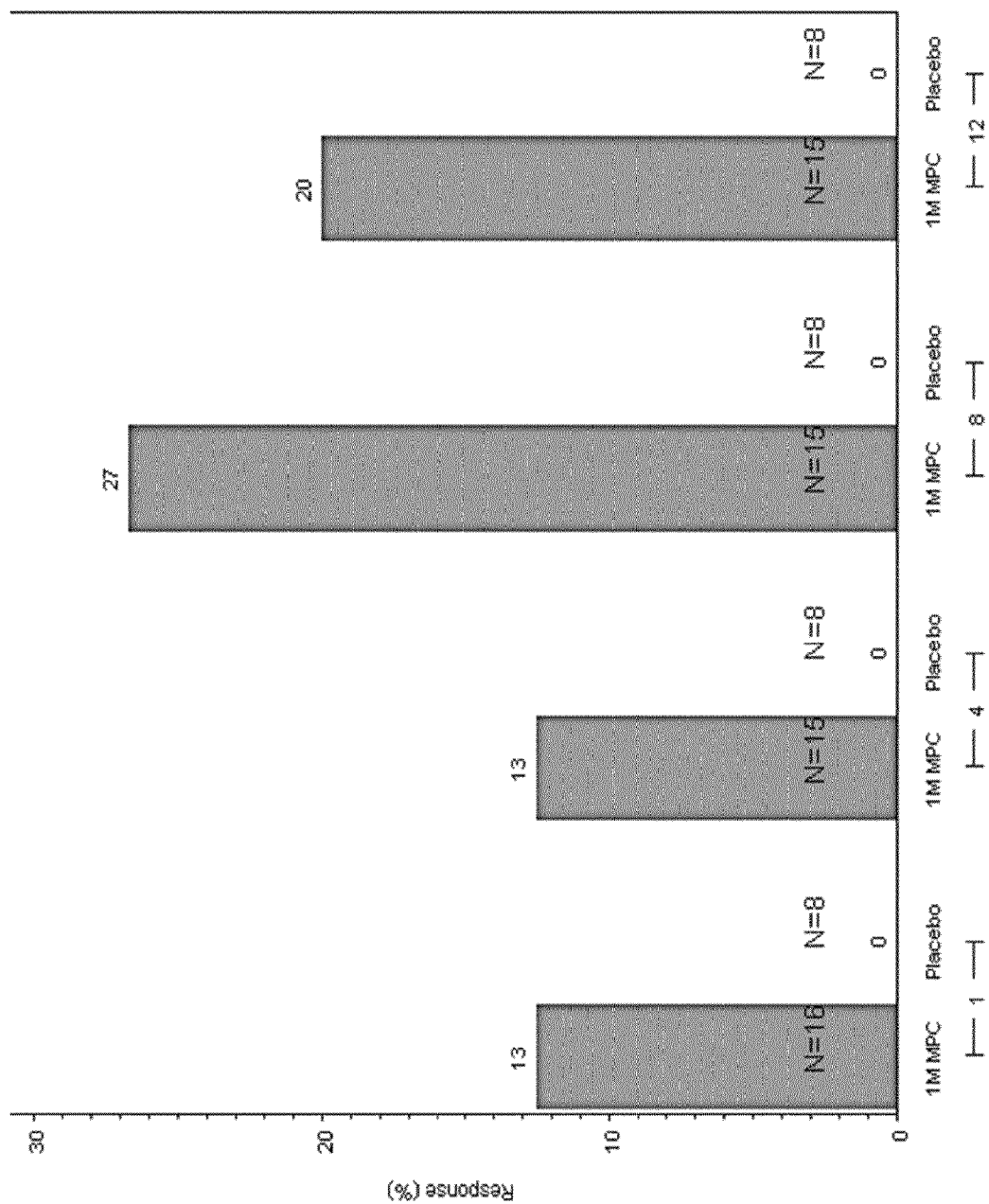
FIG. 20: ACR 70 response biologic refractory RA: 1M MPCs/kg
Figure 21:
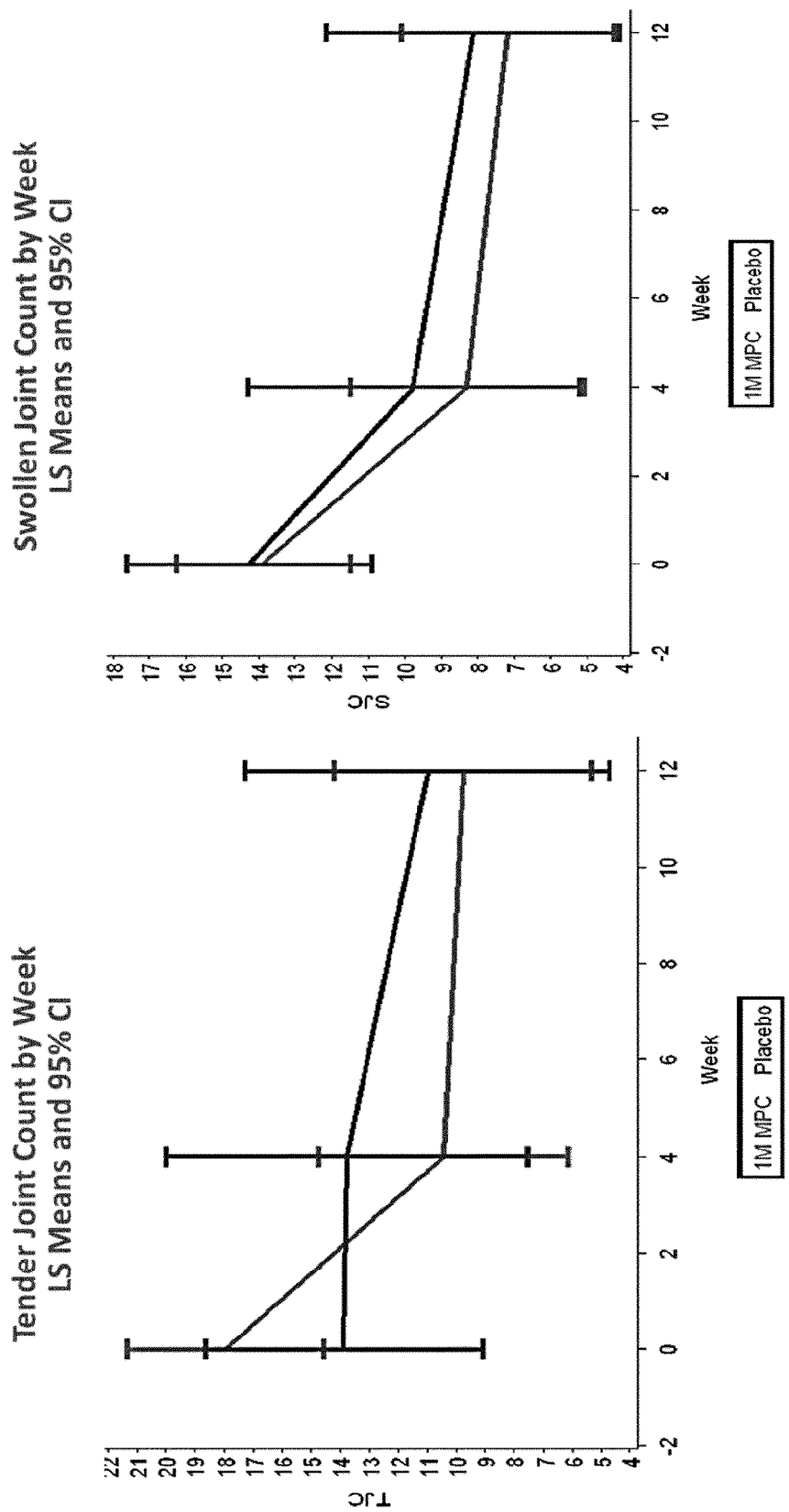
FIG. 21: ACR response over time by component; tender (TJC; left) and swollen (SJC; right) joint counts by week
Figure 22:
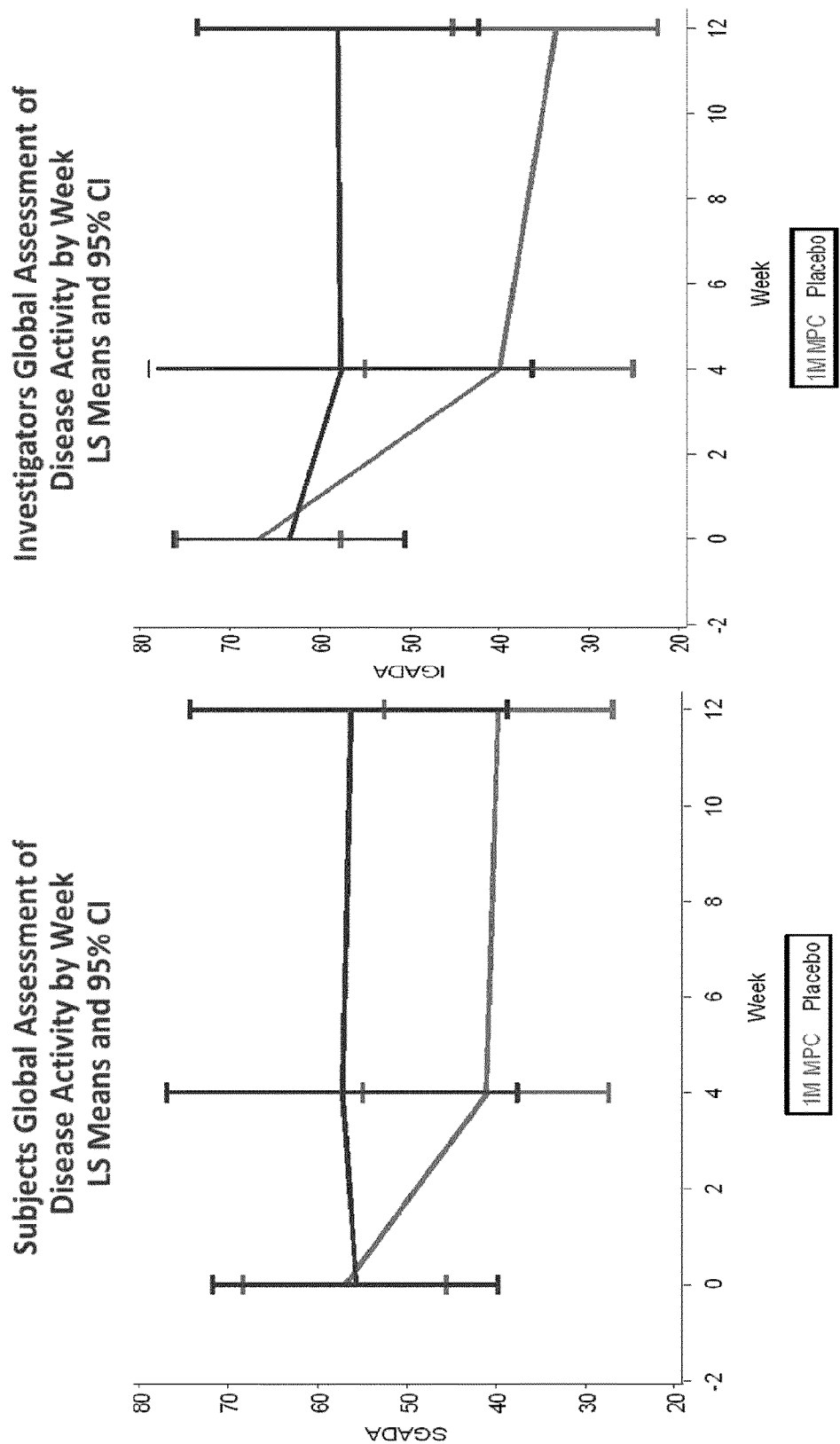
FIG. 22: ACR response over time by component; Subjects global assessment of disease activity (SGADA) by week (left); Investigators global assessment of disease activity (IGADA) by week (right)

Subjects were separated into two cohorts:
Cohort 1: MPC does (1.0 million cells/kg) [n=16] or placebo [n=8]
Cohort 2: MPC dose (2.0 million cells/kg) [n=16] or placebo [n=8]
Endpoints assessed three months post-infusion included:
TNFα; IL-6 (FIG. 17), IL-17; RANKL; MMP-1,3,9; TIMP-1, 2, 4 and osteocalcin levels. Levels were also assessed at weeks 0, 1, 2, 4, 6, 8 and 10;
ACR 20 (FIG. 18)/50 (FIG. 19)/70 (FIG. 20);
ACR core set (FIG. 21; FIG. 22);
Remission (Disease Activity Score (DAS28 (CRP))<2.6) (FIG. 23);

injected human subjects with type 2 diabetes and moderate to severe chronic kidney disease on a stable regimen of ACEi or ARB therapy for diabetic nephropathy.

Figure 25:
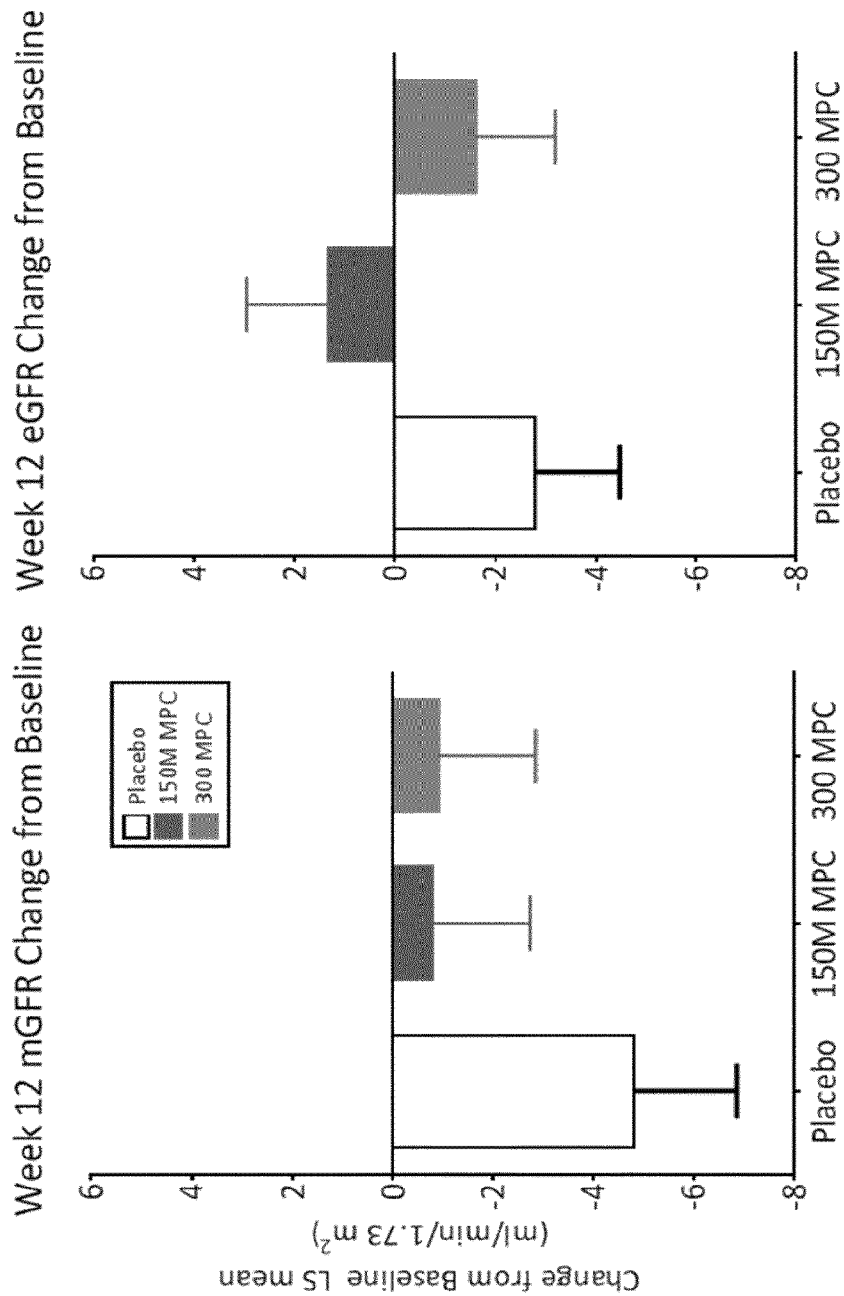
FIG. 25: Week 12 mGFR [$^{99}$Tc DTPA] and eGFR [MDRD], change from Baseline (ml/min/1.73 $m^2$).

Subjects were separated into 2 cohorts:
Cohort 1: MPC dose 1 (150 million cells) [n=10] or placebo [n=5]
Cohort 2: MPC dose 1 (300 million cells) [n=10] or placebo [n=5]
Endpoints assessed three months and 6 months post infusion:
Measured GFR (mGFR [99Tc DTPA]) (FIG. 25), estimated GFR (eGFR [MDRD]) (FIG. 25), IL-6 (FIG. 26); and serum creatinine levels;
Correlation between IL-6 and serum creatinine levels (FIG. 27).

Figure 26:
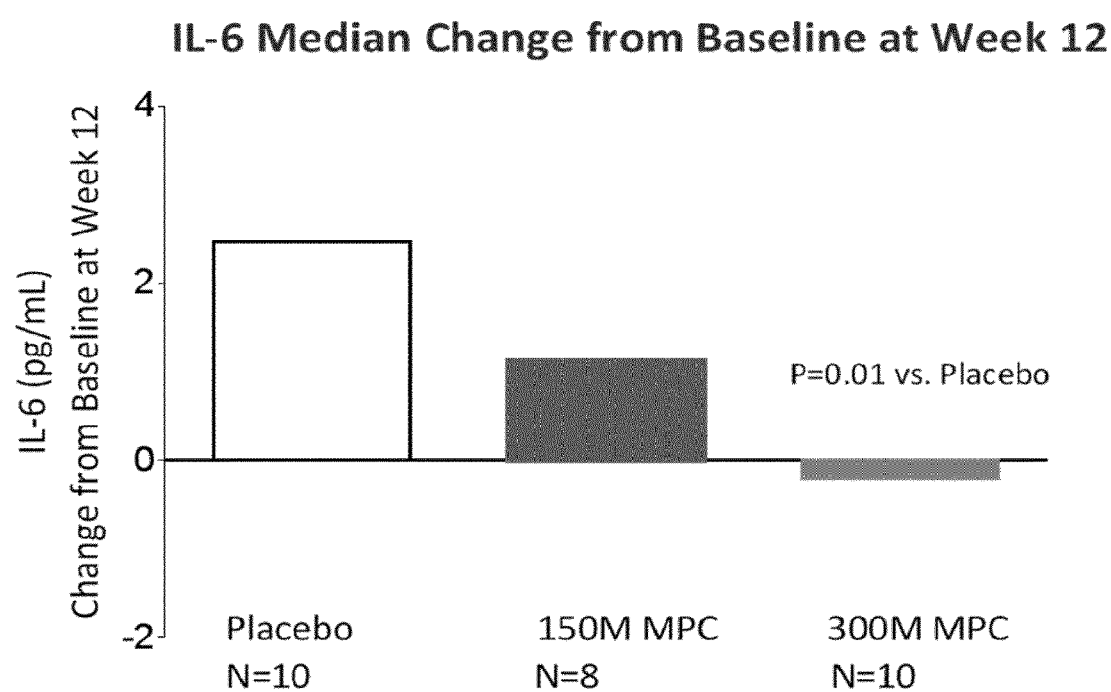
FIG. 26: IL-6 median change from baseline at week 12
Figure 27:
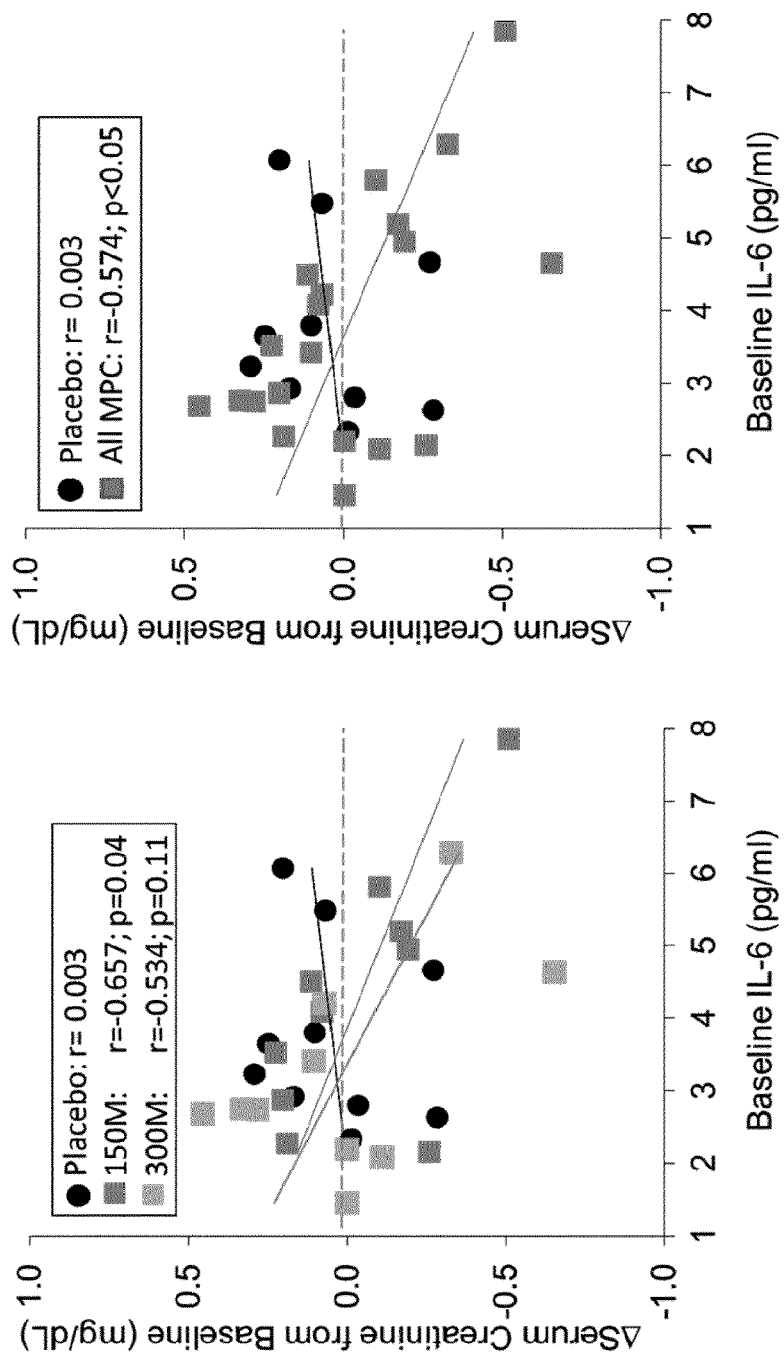
FIG. 27: Baseline IL-6 correlated with improved serum creatinine at week 12 in MPC treated patients
Figure 28:
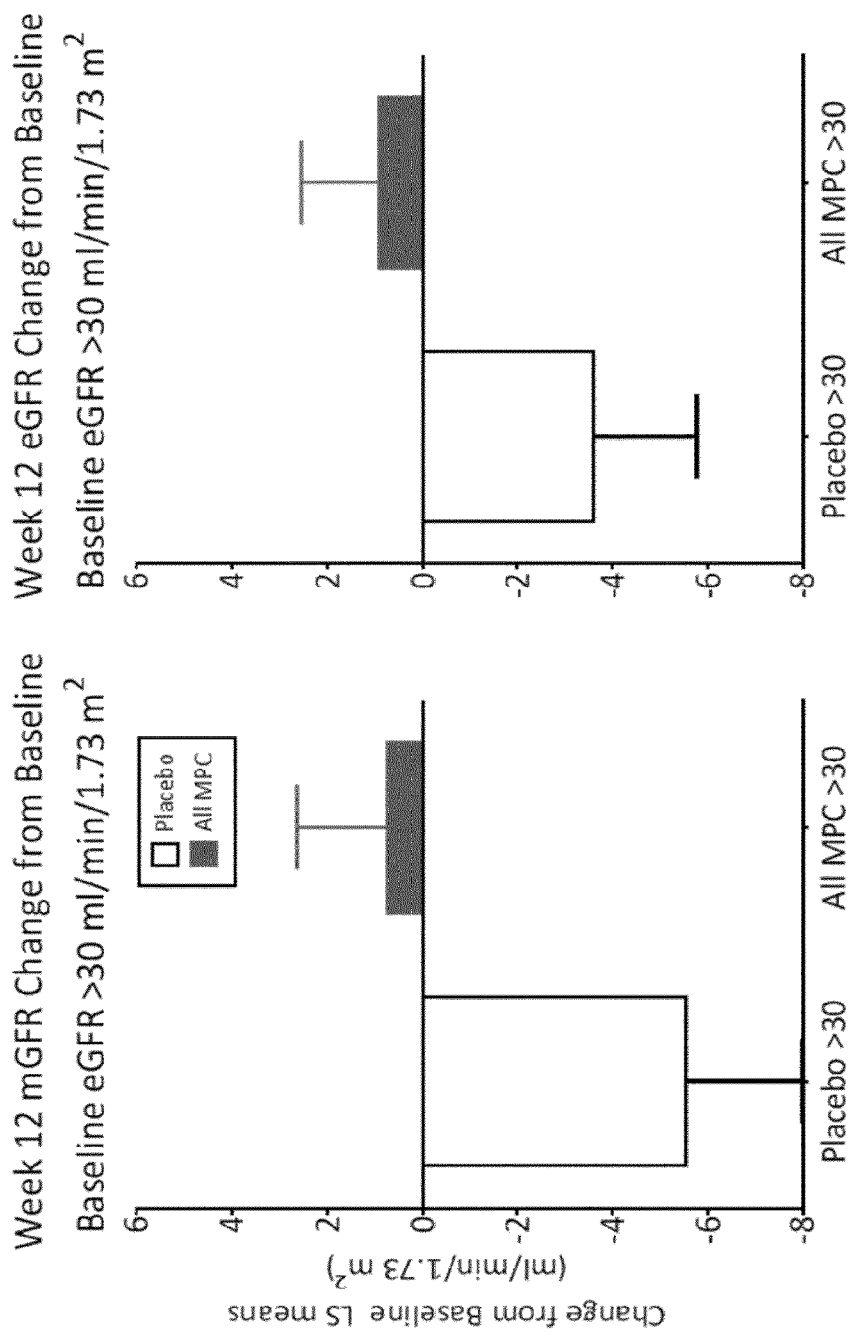
FIG. 28: Change from baseline at week 12 in mGFR and eGFR Subjects with Baseline eGFR >30 ml/min/1.73 $m^2$.

During the initial 24 week study period, there were observed trends in preservation or improvement of renal function by both measured and estimated GFR in MPC treated subjects relative to placebo:
Treatment effect was similar with both MPC doses;
More pronounced treatment effect with MPCs was in subjects with baseline eGFR >30 ml/min/1.73 m² (FIG. 28);

More pronounced MPC treatment effect with MPCs in subjects with baseline IL-6 levels above the median;

Significant correlation between baseline IL-6 levels and MPC-related improvement in serum creatinine (FIG. 27);

There was a dose-dependent change in serum IL-6 levels at 12 weeks in MPC groups vs placebo (FIG. 26).

It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

The present application claims priority from AU 2014902194 filed 10 Jun. 2014 and AU 2014902257 filed 13 Jun. 2014, the disclosures of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

The invention claimed is:

1. A method of treating an inflammatory disease in a subject, the method comprising administering to the subject a composition comprising genetically unmodified stem cells wherein said genetically unmodified stem cells express angiopoietin 1 (Ang1) and vascular endothelial growth factor (VEGF), wherein the VEGF is expressed in an amount from $0.01\ \mu g/10^6$ cells to $0.05\ \mu g/10^6$ cells.

2. The method of claim 1, wherein said genetically unmodified stem cells are mesenchymal precursor cells.

3. The method of claim 1, wherein said genetically unmodified stem cells are mesenchymal stem cells.

4. The method of claim 1, wherein the method comprises administering to the subject about $0.1 \times 10^6$ to about $3 \times 10^6$ genetically unmodified stem cells per kg body weight of to the subject.

5. The method of claim 4, wherein the method comprises administering to the subject about $2 \times 10^6$ genetically unmodified stem cells per kg body weight of the subject.

6. The method of claim 1, wherein the inflammatory disease is rheumatoid arthritis.

7. The method of claim 1, wherein said genetically unmodified stem cells are administered intravenously.

8. The method of claim 1, wherein said genetically unmodified stem cells are administered over multiple doses.

9. The method of claim 1, wherein said genetically unmodified stem cells express vascular endothelial growth factor (VEGF) in an amount less than $0.03\ \mu g/10^6$ cells.

10. The method of claim 9, wherein said genetically unmodified stem cells express vascular endothelial growth factor (VEGF) in an amount less than $0.02\ \mu g/10^6$ cells.

* * * * *